US011642063B2

(12) United States Patent
Tegg

(10) Patent No.: US 11,642,063 B2
(45) Date of Patent: May 9, 2023

(54) CURVED HIGH DENSITY ELECTRODE MAPPING CATHETER

(71) Applicant: St. Jude Medical, Cardiology Division, Inc., St. Paul, MN (US)

(72) Inventor: Troy T. Tegg, Elk River, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 600 days.

(21) Appl. No.: 16/548,487

(22) Filed: Aug. 22, 2019

(65) Prior Publication Data

US 2020/0060569 A1 Feb. 27, 2020

Related U.S. Application Data

(60) Provisional application No. 62/721,859, filed on Aug. 23, 2018.

(51) Int. Cl.
*A61B 5/287* (2021.01)
*A61B 5/00* (2006.01)
(Continued)

(52) U.S. Cl.
CPC ............ *A61B 5/287* (2021.01); *A61B 5/6858* (2013.01); *A61B 18/1492* (2013.01);
(Continued)

(58) Field of Classification Search
CPC ...... A61B 18/1492; A61B 2018/00267; A61B 2018/00351; A61B 2018/00839; A61B 2018/00577; A61B 5/287
See application file for complete search history.

(56) References Cited

U.S. PATENT DOCUMENTS

| | | | |
|---|---|---|---|
| 4,522,212 A | 6/1985 | Gelinas et al. | |
| 5,044,368 A | 9/1991 | Putz | |

(Continued)

FOREIGN PATENT DOCUMENTS

| | | |
|---|---|---|
| AU | 2015202258 A1 | 5/2015 |
| AU | 2016204351 A1 | 1/2017 |

(Continued)

OTHER PUBLICATIONS

Rao, Chepuri R.K. and Trivedi, D.C., Chemical and electrochemical depositions of platinum group metals and their applications, Coordination Chemistry Reviews, 249, (2005) pp. 613-631.

(Continued)

*Primary Examiner* — Eun Hwa Kim
(74) *Attorney, Agent, or Firm* — Kilpatrick Townsend & Stockton LLP

(57) ABSTRACT

Embodiments of the present disclosure include a medical device. The medical device can include a catheter shaft that includes a proximal end and a distal end, the catheter shaft defining a catheter shaft longitudinal axis. A flexible tip portion can be located adjacent to the distal end of the catheter shaft, the flexible tip portion comprising a flexible framework, wherein the flexible framework is curved about a transverse framework axis that is disposed transverse to the catheter shaft longitudinal axis without application of a force external to the medical device. A plurality of microelectrodes can be disposed on the flexible framework and can form a flexible array of microelectrodes adapted to conform to tissue.

10 Claims, 10 Drawing Sheets

(51) Int. Cl.
  *A61B 18/14* (2006.01)
  *A61N 1/362* (2006.01)
  *A61B 17/00* (2006.01)
  *A61B 18/00* (2006.01)

(52) U.S. Cl.
  CPC .... *A61N 1/362* (2013.01); *A61B 2017/00526* (2013.01); *A61B 2018/00267* (2013.01); *A61B 2018/00351* (2013.01); *A61B 2018/00577* (2013.01); *A61B 2018/00839* (2013.01); *A61B 2562/028* (2013.01); *A61B 2562/125* (2013.01); *A61B 2562/222* (2013.01)

(56) References Cited

U.S. PATENT DOCUMENTS

| | | | |
|---|---|---|---|
| 5,156,151 | A | 10/1992 | Imran |
| 5,224,939 | A | 7/1993 | Holman et al. |
| 5,380,301 | A | 1/1995 | Prichard et al. |
| 5,400,783 | A | 3/1995 | Pomeranz et al. |
| 5,450,846 | A | 9/1995 | Goldreyer |
| 5,456,254 | A | 10/1995 | Pietroski et al. |
| 5,465,717 | A | 11/1995 | Imran et al. |
| 5,626,136 | A | 5/1997 | Webster, Jr. |
| 5,687,723 | A | 11/1997 | Avitall |
| 5,702,438 | A | 12/1997 | Avitall |
| 5,715,817 | A | 2/1998 | Stevens-Wright et al. |
| 5,715,832 | A | 2/1998 | Koblish et al. |
| 5,827,278 | A | 10/1998 | Webster, Jr. |
| 5,836,947 | A * | 11/1998 | Fleischman ............ A61N 1/056 606/41 |
| 5,846,196 | A | 12/1998 | Siekmeyer et al. |
| 5,876,373 | A | 3/1999 | Giba et al. |
| 5,879,295 | A * | 3/1999 | Li ..................... A61B 18/1492 607/125 |
| 5,885,278 | A * | 3/1999 | Fleischman ........ A61B 18/1492 606/41 |
| 5,964,757 | A | 10/1999 | Ponzi |
| 6,029,091 | A | 2/2000 | de la Rama et al. |
| 6,071,282 | A | 6/2000 | Fleischman |
| 6,074,379 | A | 6/2000 | Prichard |
| 6,120,476 | A | 9/2000 | Fung et al. |
| 6,123,699 | A | 9/2000 | Webster, Jr. |
| 6,171,277 | B1 | 1/2001 | Ponzi |
| 6,183,463 | B1 | 2/2001 | Webster, Jr. |
| 6,198,974 | B1 | 3/2001 | Webster, Jr. |
| 6,210,407 | B1 | 4/2001 | Webster |
| 6,216,043 | B1 | 4/2001 | Swanson et al. |
| 6,233,476 | B1 | 5/2001 | Strommer et al. |
| 6,267,746 | B1 | 7/2001 | Bumbalough |
| 6,273,404 | B1 | 8/2001 | Holman et al. |
| 6,415,187 | B1 | 7/2002 | Kuzma et al. |
| 6,430,426 | B2 | 8/2002 | Avitall |
| 6,477,423 | B1 | 11/2002 | Jenkins |
| 6,491,681 | B1 | 12/2002 | Kunis et al. |
| 6,498,944 | B1 | 12/2002 | Ben-Haim et al. |
| 6,522,932 | B1 | 2/2003 | Kuzma et al. |
| 6,554,794 | B1 | 4/2003 | Mueller et al. |
| 6,652,515 | B1 | 11/2003 | Maguire et al. |
| 6,658,302 | B1 | 12/2003 | Kuzma et al. |
| 6,690,963 | B2 | 2/2004 | Ben-Haim et al. |
| 6,788,967 | B2 | 9/2004 | Ben-Haim et al. |
| 6,961,602 | B2 | 11/2005 | Fuimaono et al. |
| 7,004,937 | B2 | 2/2006 | Lentz et al. |
| 7,027,851 | B2 | 4/2006 | Mejia |
| 7,089,045 | B2 | 8/2006 | Fuimaono et al. |
| 7,099,712 | B2 | 8/2006 | Fuimaono et al. |
| 7,197,354 | B2 | 3/2007 | Sobe |
| 7,214,220 | B2 | 5/2007 | McGlinch et al. |
| 7,217,256 | B2 | 5/2007 | Di Palma |
| 7,228,164 | B2 | 6/2007 | Fuimaono et al. |
| 7,257,435 | B2 | 8/2007 | Plaza |
| 7,263,397 | B2 | 8/2007 | Hauck et al. |
| 7,386,339 | B2 | 6/2008 | Strommer et al. |
| 7,412,274 | B2 | 8/2008 | Mejia |
| 7,429,261 | B2 | 9/2008 | Kunis et al. |
| 7,536,218 | B2 | 5/2009 | Govari et al. |
| 7,561,907 | B2 | 7/2009 | Fuimaono et al. |
| 7,608,063 | B2 | 10/2009 | Le et al. |
| 7,625,365 | B2 | 12/2009 | McGlinch et al. |
| 7,666,204 | B2 | 2/2010 | Thornton et al. |
| 7,959,601 | B2 | 6/2011 | McDaniel et al. |
| 7,985,215 | B2 | 7/2011 | Guo et al. |
| 8,103,327 | B2 | 1/2012 | Harlev et al. |
| 8,137,321 | B2 | 3/2012 | Argentine |
| 8,157,848 | B2 | 4/2012 | Zhang et al. |
| 8,221,390 | B2 | 7/2012 | Pal et al. |
| 8,271,099 | B1 | 9/2012 | Swanson |
| 8,273,016 | B2 | 9/2012 | O'sullivan |
| 8,364,234 | B2 | 1/2013 | Kordis et al. |
| 8,376,990 | B2 | 2/2013 | Ponzi et al. |
| 8,391,947 | B2 | 3/2013 | Urman et al. |
| 8,447,377 | B2 | 5/2013 | Harlev et al. |
| 8,486,063 | B2 | 7/2013 | Werneth et al. |
| 8,560,086 | B2 | 10/2013 | Just et al. |
| 8,565,894 | B2 | 10/2013 | Vetter et al. |
| 8,603,069 | B2 | 12/2013 | Selkee |
| 8,608,703 | B2 | 12/2013 | Riles et al. |
| 8,649,880 | B1 | 2/2014 | Parker, Jr. |
| 8,700,120 | B2 | 4/2014 | Koblish |
| 8,706,193 | B2 | 4/2014 | Govari et al. |
| 8,744,599 | B2 | 6/2014 | Tegg |
| 8,755,861 | B2 | 6/2014 | Harlev et al. |
| 8,777,929 | B2 | 7/2014 | Schneider et al. |
| 8,792,962 | B2 | 7/2014 | Esguerra et al. |
| 8,795,504 | B2 | 8/2014 | Petrossians et al. |
| 8,814,824 | B2 | 8/2014 | Kauphusman et al. |
| 8,814,825 | B2 | 8/2014 | Tegg et al. |
| 8,882,705 | B2 | 11/2014 | McDaniel et al. |
| 8,894,610 | B2 | 11/2014 | Macnamara et al. |
| 8,903,508 | B2 | 12/2014 | Feler |
| 8,996,091 | B2 | 3/2015 | de la Rama et al. |
| 9,017,308 | B2 | 4/2015 | Klisch et al. |
| 9,033,917 | B2 | 5/2015 | Magana et al. |
| 9,044,245 | B2 | 6/2015 | Condie et al. |
| 9,050,010 | B2 | 6/2015 | Bui et al. |
| 9,101,733 | B2 | 8/2015 | McDaniel |
| 9,204,929 | B2 | 12/2015 | Solis |
| 9,216,056 | B2 | 12/2015 | Datta et al. |
| 9,247,990 | B2 | 2/2016 | Kauphusman et al. |
| 9,326,815 | B2 | 5/2016 | Watson |
| 9,339,631 | B2 | 5/2016 | Graham et al. |
| 9,433,751 | B2 | 9/2016 | Ponzi et al. |
| 9,433,752 | B2 | 9/2016 | Jimenez et al. |
| 9,468,495 | B2 | 10/2016 | Kunis et al. |
| 9,486,280 | B2 | 11/2016 | Koblish et al. |
| 9,486,282 | B2 | 11/2016 | Solis |
| 9,532,703 | B2 | 1/2017 | Huszar et al. |
| 9,539,413 | B2 | 1/2017 | Ogle |
| 9,649,158 | B2 | 5/2017 | Datta et al. |
| 9,687,166 | B2 | 6/2017 | Subramaniam et al. |
| 9,693,733 | B2 | 7/2017 | Altmann et al. |
| 9,694,159 | B2 | 7/2017 | Schneider et al. |
| 9,694,161 | B2 | 7/2017 | Selkee |
| 9,713,418 | B2 | 7/2017 | Huszar et al. |
| 9,788,895 | B2 | 10/2017 | Solis |
| 9,820,664 | B2 | 11/2017 | Hoitink et al. |
| 9,833,608 | B2 | 12/2017 | Masson |
| 9,844,645 | B2 | 12/2017 | Pai et al. |
| 9,848,795 | B2 | 12/2017 | Marecki et al. |
| 9,907,480 | B2 | 3/2018 | Basu et al. |
| 9,919,132 | B2 | 3/2018 | Tegg et al. |
| 9,949,656 | B2 | 4/2018 | Wu et al. |
| 9,986,949 | B2 | 6/2018 | Govari et al. |
| 10,004,877 | B2 | 6/2018 | Tegg |
| 10,034,637 | B2 | 7/2018 | Harlev et al. |
| 10,052,457 | B2 | 8/2018 | Nguyen et al. |
| 10,065,019 | B2 | 9/2018 | Hamuro et al. |
| 10,099,036 | B2 | 10/2018 | Heideman et al. |
| 10,118,022 | B2 | 11/2018 | Helgeson et al. |
| 10,143,394 | B2 | 12/2018 | Solis |
| 10,285,610 | B2 | 5/2019 | Wu |
| 10,322,261 | B2 | 6/2019 | Pai et al. |
| 10,362,952 | B2 | 7/2019 | Basu et al. |

(56) References Cited

U.S. PATENT DOCUMENTS

| | | |
|---|---|---|
| 10,362,954 B2 | 7/2019 | de la Rama et al. |
| 10,376,170 B2 | 8/2019 | Quinn et al. |
| 10,384,036 B2 | 8/2019 | Romoscanu |
| 10,398,500 B2 | 9/2019 | Huszar et al. |
| 10,478,325 B2 | 11/2019 | Syed |
| 10,506,938 B2 | 12/2019 | Wu et al. |
| 10,537,259 B2 | 1/2020 | Wu et al. |
| 10,542,899 B2 | 1/2020 | Wu et al. |
| 10,556,091 B2 | 2/2020 | Truhler et al. |
| 10,575,742 B2 | 3/2020 | Wu et al. |
| 10,575,745 B2 | 3/2020 | Solis |
| 10,578,737 B2 | 3/2020 | Gliner et al. |
| 10,595,738 B2 | 3/2020 | Sterrett et al. |
| 10,595,740 B2 | 3/2020 | Hoitink et al. |
| 10,602,948 B2 | 3/2020 | Wu et al. |
| 10,646,692 B2 | 5/2020 | Tegg et al. |
| 10,653,423 B2 | 5/2020 | Starnes |
| 10,702,177 B2 | 7/2020 | Aujla |
| 10,702,677 B2 | 7/2020 | Okamura et al. |
| 10,737,060 B2 | 8/2020 | Gupta et al. |
| 10,835,712 B2 | 11/2020 | Wada |
| 10,842,990 B2 | 11/2020 | de la Rama et al. |
| 10,857,349 B2 | 12/2020 | de la Rama et al. |
| 10,869,992 B2 | 12/2020 | Pai et al. |
| 10,898,685 B2 | 1/2021 | Tegg |
| 10,912,925 B2 | 2/2021 | Houck |
| 10,945,626 B2 | 3/2021 | Fuentes-ortega et al. |
| 10,946,167 B2 | 3/2021 | Mintz et al. |
| 10,953,196 B2 | 3/2021 | Raab et al. |
| 10,959,636 B2 | 3/2021 | Dahlen et al. |
| 10,966,623 B2 | 4/2021 | Wu et al. |
| 10,966,753 B2 | 4/2021 | Coyle et al. |
| 10,967,150 B2 | 4/2021 | Helgeson et al. |
| 10,987,045 B2 | 4/2021 | Basu et al. |
| 11,033,715 B2 | 6/2021 | Beeckler et al. |
| 11,039,772 B2 | 6/2021 | Wu et al. |
| 11,039,773 B2 | 6/2021 | Sterrett et al. |
| 11,083,400 B2 | 8/2021 | Hoitink et al. |
| 11,116,436 B2 | 9/2021 | Wu et al. |
| 11,116,476 B2 | 9/2021 | Buesseler et al. |
| 11,123,051 B2 | 9/2021 | Van Der Linde et al. |
| 11,141,568 B2 | 10/2021 | Hsueh et al. |
| 11,160,482 B2 | 11/2021 | Solis |
| 11,172,858 B2 | 11/2021 | Olson et al. |
| 11,272,886 B2 | 3/2022 | Harlev et al. |
| 2001/0047129 A1 | 11/2001 | Hall et al. |
| 2002/0165484 A1 | 11/2002 | Bowe et al. |
| 2003/0093069 A1 | 5/2003 | Panescu et al. |
| 2003/0120328 A1 | 6/2003 | Jenkins et al. |
| 2004/0186546 A1 | 9/2004 | Mandrusov et al. |
| 2005/0159741 A1 | 7/2005 | Paul et al. |
| 2007/0123852 A1 | 5/2007 | Deem et al. |
| 2007/0219546 A1 | 9/2007 | Mody et al. |
| 2008/0243214 A1 | 10/2008 | Koblish |
| 2008/0312521 A1 | 12/2008 | Solomon |
| 2008/0319418 A1 | 12/2008 | Chong |
| 2009/0171274 A1 | 7/2009 | Harlev et al. |
| 2009/0198300 A1 | 8/2009 | Zhang et al. |
| 2009/0240248 A1 | 9/2009 | Deford et al. |
| 2010/0016848 A1 | 1/2010 | Desai |
| 2010/0286684 A1 | 11/2010 | Hata et al. |
| 2011/0106074 A1 | 5/2011 | Kunis et al. |
| 2011/0118726 A1 | 5/2011 | de la Rama et al. |
| 2011/0160721 A1 | 6/2011 | Wang et al. |
| 2011/0190732 A1 | 8/2011 | Majercak et al. |
| 2011/0313417 A1 | 12/2011 | de la Rama et al. |
| 2012/0172697 A1 | 7/2012 | Urman et al. |
| 2012/0271302 A1 | 10/2012 | Behl et al. |
| 2012/0296232 A1 | 11/2012 | Ng |
| 2013/0012938 A1 | 1/2013 | Asirvatham et al. |
| 2013/0253504 A1 | 9/2013 | Fang |
| 2013/0274582 A1 | 10/2013 | Afonso et al. |
| 2014/0100639 A1 | 4/2014 | Lee et al. |
| 2014/0142408 A1 | 5/2014 | de la Rama et al. |
| 2014/0200639 A1 | 7/2014 | de la Rama |
| 2014/0269602 A1 | 9/2014 | Kawagishi |
| 2014/0288552 A1 | 9/2014 | Kunis et al. |
| 2014/0296846 A1 | 10/2014 | Huszar et al. |
| 2014/0296902 A1 | 10/2014 | Huszar et al. |
| 2014/0316496 A1 | 10/2014 | Masson et al. |
| 2014/0336636 A1 | 11/2014 | Huszar et al. |
| 2014/0350564 A1 | 11/2014 | Huszar et al. |
| 2015/0105645 A1 | 4/2015 | Subramaniam et al. |
| 2015/0119911 A1 | 4/2015 | Mckenzie |
| 2015/0141785 A1 | 5/2015 | Hayam et al. |
| 2015/0159741 A1 | 6/2015 | Versteyhe et al. |
| 2015/0351652 A1 | 12/2015 | Marecki et al. |
| 2015/0374252 A1* | 12/2015 | de la Rama ........ A61B 18/1492 606/41 |
| 2016/0073960 A1 | 3/2016 | Jung et al. |
| 2016/0143588 A1 | 5/2016 | Hoitink et al. |
| 2016/0213423 A1 | 7/2016 | Kauphusman et al. |
| 2016/0213916 A1 | 7/2016 | de la Rama |
| 2016/0278851 A1 | 9/2016 | Mannion et al. |
| 2016/0317094 A1 | 11/2016 | Byrd et al. |
| 2016/0331471 A1 | 11/2016 | Deno et al. |
| 2016/0331933 A1 | 11/2016 | Knutsen |
| 2016/0374582 A1 | 12/2016 | Wu et al. |
| 2016/0374753 A1 | 12/2016 | Wu et al. |
| 2017/0000365 A1 | 1/2017 | Wu et al. |
| 2017/0042449 A1 | 2/2017 | Deno et al. |
| 2017/0049348 A1 | 2/2017 | Deno et al. |
| 2017/0112404 A1 | 4/2017 | de la Rama et al. |
| 2017/0112405 A1* | 4/2017 | Sterrett ................ A61B 18/14 |
| 2017/0273738 A1 | 9/2017 | Wu |
| 2017/0319269 A1 | 11/2017 | Oliverius et al. |
| 2017/0367756 A1 | 12/2017 | Sliwa et al. |
| 2018/0042667 A1 | 2/2018 | Pappone et al. |
| 2018/0056038 A1 | 3/2018 | Aujla |
| 2018/0070845 A1 | 3/2018 | Hoitink et al. |
| 2018/0085064 A1 | 3/2018 | Auerbach et al. |
| 2018/0116539 A1 | 5/2018 | Olson et al. |
| 2018/0161093 A1 | 6/2018 | Basu et al. |
| 2018/0193089 A1 | 7/2018 | Wu |
| 2018/0229030 A1 | 8/2018 | Dubuclet et al. |
| 2018/0235496 A1 | 8/2018 | Wu et al. |
| 2018/0303361 A1 | 10/2018 | Wu et al. |
| 2018/0335519 A1 | 11/2018 | Gliner et al. |
| 2018/0369574 A1 | 12/2018 | Dubuclet et al. |
| 2019/0009052 A1 | 1/2019 | Oliverius et al. |
| 2019/0125378 A1 | 5/2019 | Shelton, IV et al. |
| 2019/0175043 A1 | 6/2019 | Wu et al. |
| 2019/0192826 A1 | 6/2019 | Wada |
| 2019/0239812 A1 | 8/2019 | Botzer et al. |
| 2020/0077912 A1 | 3/2020 | Wu et al. |
| 2020/0121894 A1 | 4/2020 | Prabhu et al. |
| 2020/0138378 A1 | 5/2020 | de la Rama et al. |
| 2020/0155021 A1 | 5/2020 | Wu et al. |
| 2020/0214635 A1 | 7/2020 | Dahlen et al. |
| 2020/0221966 A1 | 7/2020 | Wu et al. |
| 2020/0229727 A1 | 7/2020 | Hoitink et al. |
| 2020/0253496 A1 | 8/2020 | Deno et al. |
| 2020/0329989 A1 | 10/2020 | Aujla |
| 2020/0405166 A1 | 12/2020 | Wu et al. |
| 2021/0038860 A1 | 2/2021 | Mintz et al. |
| 2021/0145342 A1 | 5/2021 | Wang |
| 2021/0153932 A1 | 5/2021 | Voth et al. |
| 2021/0187246 A1 | 6/2021 | Houck |
| 2021/0204871 A1 | 7/2021 | Goedeke et al. |
| 2021/0228137 A1 | 7/2021 | Aujla |
| 2021/0268234 A1 | 9/2021 | Helgeson et al. |
| 2021/0298656 A1 | 9/2021 | Wu et al. |
| 2021/0361216 A1 | 11/2021 | Hoitink et al. |
| 2021/0401345 A1 | 12/2021 | Wu et al. |
| 2022/0023594 A1 | 1/2022 | Pai |
| 2022/0054066 A1 | 2/2022 | Solis |
| 2022/0061727 A1 | 3/2022 | Olson et al. |

FOREIGN PATENT DOCUMENTS

| | | |
|---|---|---|
| AU | 2016204353 A1 | 1/2017 |
| AU | 2016204355 A1 | 1/2017 |
| CA | 2934209 A1 | 12/2016 |
| CA | 2934211 A1 | 12/2016 |

(56) References Cited

FOREIGN PATENT DOCUMENTS

| | | |
|---|---|---|
| CA | 2934214 A1 | 12/2016 |
| CN | 101797181 A | 8/2010 |
| CN | 101927053 B | 1/2015 |
| CN | 103157168 B | 4/2015 |
| CN | 105960201 A | 9/2016 |
| CN | 106859765 A | 6/2017 |
| CN | 206880930 U | 1/2018 |
| CN | 104958824 B | 12/2018 |
| CN | 104434083 B | 4/2019 |
| CN | 104968261 B | 5/2019 |
| CN | 105592778 B | 7/2019 |
| CN | 110536646 A | 12/2019 |
| CN | 110604860 A | 12/2019 |
| CN | 111225627 A | 6/2020 |
| CN | 111432739 A | 7/2020 |
| CN | 111657866 A | 9/2020 |
| CN | 106264715 B | 11/2020 |
| CN | 106264716 B | 11/2020 |
| CN | 112040861 A | 12/2020 |
| CN | 106308790 B | 6/2021 |
| CN | 107529958 B | 7/2021 |
| CN | 109310469 B | 7/2021 |
| CN | 109641121 B | 9/2021 |
| CN | 109952123 B | 9/2021 |
| CN | 110545874 B | 9/2021 |
| CN | 110559544 B | 9/2021 |
| CN | 113425304 A | 9/2021 |
| CN | 105615994 B | 10/2021 |
| CN | 109963610 B | 11/2021 |
| CN | 108289709 B | 3/2022 |
| EP | 0779059 A1 | 6/1997 |
| EP | 0889744 B1 | 1/2004 |
| EP | 1254641 B1 | 11/2008 |
| EP | 1690564 B1 | 4/2009 |
| EP | 1723981 B1 | 8/2010 |
| EP | 2135634 B1 | 10/2011 |
| EP | 2018203 B1 | 6/2012 |
| EP | 1814450 B1 | 1/2013 |
| EP | 2269532 B1 | 3/2013 |
| EP | 2664295 A1 | 11/2013 |
| EP | 2604306 B1 | 1/2014 |
| EP | 2732843 A1 | 5/2014 |
| EP | 2747680 A2 | 7/2014 |
| EP | 2752153 A1 | 7/2014 |
| EP | 2907462 A1 | 8/2015 |
| EP | 2915555 A1 | 9/2015 |
| EP | 1968679 B1 | 9/2016 |
| EP | 2241279 B1 | 9/2016 |
| EP | 2796103 B1 | 2/2017 |
| EP | 3222209 A1 | 9/2017 |
| EP | 2792322 B1 | 10/2017 |
| EP | 2792323 B1 | 10/2017 |
| EP | 3115076 A4 | 10/2017 |
| EP | 3117863 A4 | 10/2017 |
| EP | 3287092 A1 | 2/2018 |
| EP | 3111871 B1 | 3/2018 |
| EP | 3111872 B1 | 4/2018 |
| EP | 3057488 B1 | 5/2018 |
| EP | 2848226 B1 | 7/2018 |
| EP | 3345540 A1 | 7/2018 |
| EP | 3363397 A1 | 8/2018 |
| EP | 3391928 A1 | 10/2018 |
| EP | 3122276 B1 | 11/2018 |
| EP | 3398549 A1 | 11/2018 |
| EP | 3403571 A1 | 11/2018 |
| EP | 1759668 B1 | 12/2018 |
| EP | 3037122 B1 | 12/2018 |
| EP | 2234537 B1 | 1/2019 |
| EP | 2569040 B1 | 2/2019 |
| EP | 3023052 B1 | 3/2019 |
| EP | 3466363 A1 | 4/2019 |
| EP | 2249919 B1 | 5/2019 |
| EP | 2550989 B1 | 6/2019 |
| EP | 3512589 A1 | 7/2019 |
| EP | 3527125 A1 | 8/2019 |
| EP | 3531903 A1 | 9/2019 |
| EP | 3581229 A1 | 12/2019 |
| EP | 3434218 B1 | 2/2020 |
| EP | 2908723 B1 | 3/2020 |
| EP | 3114987 B1 | 8/2020 |
| EP | 3178516 B1 | 9/2020 |
| EP | 3738508 A1 | 11/2020 |
| EP | 3738509 A1 | 11/2020 |
| EP | 3340916 B1 | 12/2020 |
| EP | 3579908 B1 | 12/2020 |
| EP | 3749195 A1 | 12/2020 |
| EP | 3750475 A1 | 12/2020 |
| EP | 3768185 A1 | 1/2021 |
| EP | 2155301 B1 | 4/2021 |
| EP | 3432820 B1 | 4/2021 |
| EP | 3476331 B1 | 5/2021 |
| EP | 3579758 B1 | 5/2021 |
| EP | 2809254 B1 | 6/2021 |
| EP | 3508245 B1 | 7/2021 |
| EP | 3858277 A1 | 8/2021 |
| EP | 3892221 A1 | 10/2021 |
| EP | 3932343 A4 | 1/2022 |
| EP | 3791820 B9 | 4/2022 |
| IL | 246415 B | 12/2019 |
| IN | 201614021431 A | 12/2016 |
| IN | 201614021432 A | 12/2016 |
| IN | 201614021450 A | 12/2016 |
| JP | 2009500052 A | 1/2009 |
| JP | 2010057943 A | 3/2010 |
| JP | 4545384 B2 | 7/2010 |
| JP | 4887810 B2 | 2/2012 |
| JP | 4940332 B2 | 3/2012 |
| JP | 2012055602 A | 3/2012 |
| JP | 2012130392 A | 7/2012 |
| JP | 2012200509 A | 10/2012 |
| JP | 5154031 B2 | 2/2013 |
| JP | 5193190 B2 | 5/2013 |
| JP | 5372314 B2 | 12/2013 |
| JP | 2014014713 A | 1/2014 |
| JP | 5550150 B2 | 5/2014 |
| JP | 5762697 B2 | 6/2015 |
| JP | 5856712 B2 | 2/2016 |
| JP | 5908270 B2 | 4/2016 |
| JP | 5944331 B2 | 7/2016 |
| JP | 6050522 B2 | 12/2016 |
| JP | 2017012750 A | 1/2017 |
| JP | 2017012755 A | 1/2017 |
| JP | 2017038919 A | 2/2017 |
| JP | 2017051211 A | 3/2017 |
| JP | 2017104552 A | 6/2017 |
| JP | 6246742 B2 | 12/2017 |
| JP | 6342524 B2 | 6/2018 |
| JP | 6434495 B2 | 12/2018 |
| JP | 6445509 B2 | 12/2018 |
| JP | 6445742 B1 | 12/2018 |
| JP | 6466114 B2 | 2/2019 |
| JP | 6515084 B2 | 4/2019 |
| JP | 6528010 B1 | 5/2019 |
| JP | 6655655 B2 | 2/2020 |
| JP | 6776021 B2 | 10/2020 |
| JP | 6776025 B2 | 10/2020 |
| JP | 6786275 B2 | 11/2020 |
| JP | 6821812 B2 | 1/2021 |
| JP | 2021007772 A | 1/2021 |
| JP | 2021501011 A | 1/2021 |
| JP | 6843502 B2 | 3/2021 |
| JP | 6894004 B2 | 6/2021 |
| JP | 6920312 B2 | 8/2021 |
| JP | 6926306 B2 | 8/2021 |
| JP | 6932484 B2 | 8/2021 |
| JP | 6936872 B2 | 9/2021 |
| JP | 2021523755 A | 9/2021 |
| JP | 6980386 B2 | 11/2021 |
| JP | 2022020838 A | 2/2022 |
| RU | 2016124794 A | 12/2017 |
| RU | 2016124801 A | 12/2017 |
| RU | 2016125763 A | 1/2018 |
| WO | 9843530 A1 | 10/1998 |
| WO | 0168178 A1 | 9/2001 |

(56) References Cited

FOREIGN PATENT DOCUMENTS

| | | |
|---|---|---|
| WO | 2005114720 A2 | 12/2005 |
| WO | 2007001981 A2 | 1/2007 |
| WO | 2008091197 A1 | 7/2008 |
| WO | 2008157399 A1 | 12/2008 |
| WO | 2011075328 A1 | 6/2011 |
| WO | 2012092016 A1 | 7/2012 |
| WO | 2014113612 A1 | 7/2014 |
| WO | 2015002787 A1 | 1/2015 |
| WO | 2015057521 A1 | 4/2015 |
| WO | 2015095577 A1 | 6/2015 |
| WO | 2015130824 A1 | 9/2015 |
| WO | 2016001015 A1 | 1/2016 |
| WO | 2017070559 A1 | 4/2017 |
| WO | 2017098198 A1 | 6/2017 |
| WO | 2018053148 A1 | 3/2018 |
| WO | 2018053164 A1 | 3/2018 |
| WO | 2018136741 A1 | 7/2018 |
| WO | 2019195439 A1 | 10/2019 |

OTHER PUBLICATIONS

Sheela G., et al., Electrodeposition of Iridium, Bulletin of Electrochemistry, 15 (5-6) May-Jun. 1999, pp. 208-210.

Wu, Feng, et al., Electrodeposition of Platinum-Iridium Alloy on Nickel-Base Single-Crystal Superalloy TMS75, Surface and Coatings Technology vol. 184, Issue 1, Jun. 1, 2004.

Baumgartner, M.E. and Raub, CH. J., The Electrodeposition of Platinum and Platinum Alloys, Platinum Metals Review, 1988, 32, (4), 188-197.

Ohno, Izumi, Electroless Deposition of Palladium and Platinum, Modern Electroplating, 5th Edition, Edited by Mordechay Schlesinger and Milan Paunovic, Copyright 2010, John Wiley & Sons, Inc. Chp 20, 477-482.

Electroplating the Platinum Metals—A Recent Survey of Processes and Applications, Platinum Metals Rev., 1970, 14, (3) pp. 93-94.

Yingna Wu et al., Characterization of Electroplated Platinum-Iridium Alloys on the Nickel-Base Single Crystal Superalloy, Materials Transactions, vol. 46, No. 10 (2005) pp. 2176-2179.

\* cited by examiner

CURVED HIGH DENSITY ELECTRODE MAPPING CATHETER

CROSS-REFERENCE TO RELATED APPLICATIONS

This application claims the benefit of U.S. provisional application No. 62/721,859, filed 23 Aug. 2018, which is hereby incorporated by reference as though fully set forth herein.

a. FIELD OF THE DISCLOSURE

This disclosure relates to a curved high density electrode mapping catheter.

b. BACKGROUND ART

Catheters have been used for cardiac medical procedures for many years. Catheters can be used, for example, to diagnose and treat cardiac arrhythmias, while positioned at a specific location within a body that is otherwise inaccessible without a more invasive procedure.

Conventional mapping catheters may include, for example, a plurality of adjacent ring electrodes encircling the longitudinal axis of the catheter and constructed from platinum or some other metal. These ring electrodes are relatively rigid. Similarly, conventional ablation catheters may comprise a relatively rigid tip electrode for delivering therapy (e.g., delivering RF ablation energy) and may also include a plurality of adjacent ring electrodes. It can be difficult to maintain good electrical contact with cardiac tissue when using these conventional catheters and their relatively rigid (or nonconforming), electrodes, especially when sharp gradients and undulations are present.

Whether mapping or forming lesions in a heart, the beating of the heart, especially if erratic or irregular, complicates matters, making it difficult to keep adequate contact between electrodes and tissue for a sufficient length of time. These problems are exacerbated on contoured or trabeculated surfaces. If the contact between the electrodes and the tissue cannot be sufficiently maintained, quality lesions or accurate mapping are unlikely to result.

The foregoing discussion is intended only to illustrate the present field and should not be taken as a disavowal of claim scope.

BRIEF SUMMARY

Various embodiments herein provide a medical device. The medical device can include a catheter shaft that includes a proximal end and a distal end, the catheter shaft defining a catheter shaft longitudinal axis. A flexible tip portion can be located adjacent to the distal end of the catheter shaft, the flexible tip portion comprising a flexible framework, wherein the flexible framework is curved about a transverse framework axis that is disposed transverse to the catheter shaft longitudinal axis without application of a force external to the medical device. A plurality of microelectrodes can be disposed on the flexible framework and can form a flexible array of microelectrodes adapted to conform to tissue.

Various embodiments herein provide a medical device. The medical device can include a catheter shaft comprising a proximal end and a distal end, the catheter shaft defining a central lumen and a catheter shaft longitudinal axis extending therethrough. A flexible tip portion can be located adjacent to the distal end of the catheter shaft, the flexible tip portion comprising a flexible framework. The flexible framework can include a first inboard transition arm, second inboard transition arm, first outboard transition arm, and second outboard transition arm. Each of the first inboard transition arm, second inboard transition arm, first outboard transition arm, and second outboard transition arm extend along a respective transition arm curved axis without application of a force external to the medical device, each of the transition arms being connected at their distal ends via a junction. Each respective transition arm curved axis can be disposed about a transverse framework axis that is disposed transverse to the catheter shaft longitudinal axis. The medical device can include a tether that includes a tether proximal end and a tether distal end, wherein the tether distal end is connected to the junction and the tether proximal end extends through the central lumen. A plurality of microelectrodes can be disposed on the flexible framework and can form a flexible array of microelectrodes adapted to conform to tissue.

Various embodiments herein provide a catheter. The catheter can include a proximal end and a distal end, the catheter shaft defining a catheter shaft longitudinal axis extending therethrough. The catheter can include a basket assembly disposed at a distal end of the catheter shaft. The basket assembly can include a plurality of splines. The basket catheter can include a plurality of electrodes disposed on each one of the plurality of splines, wherein a distance between adjacent electrodes on each one of the splines is of a first distance and a distance between corresponding electrodes disposed on adjacent splines is of a second distance, wherein the first distance and the second distance are equal.

DETAILED DESCRIPTION

Figure 1:
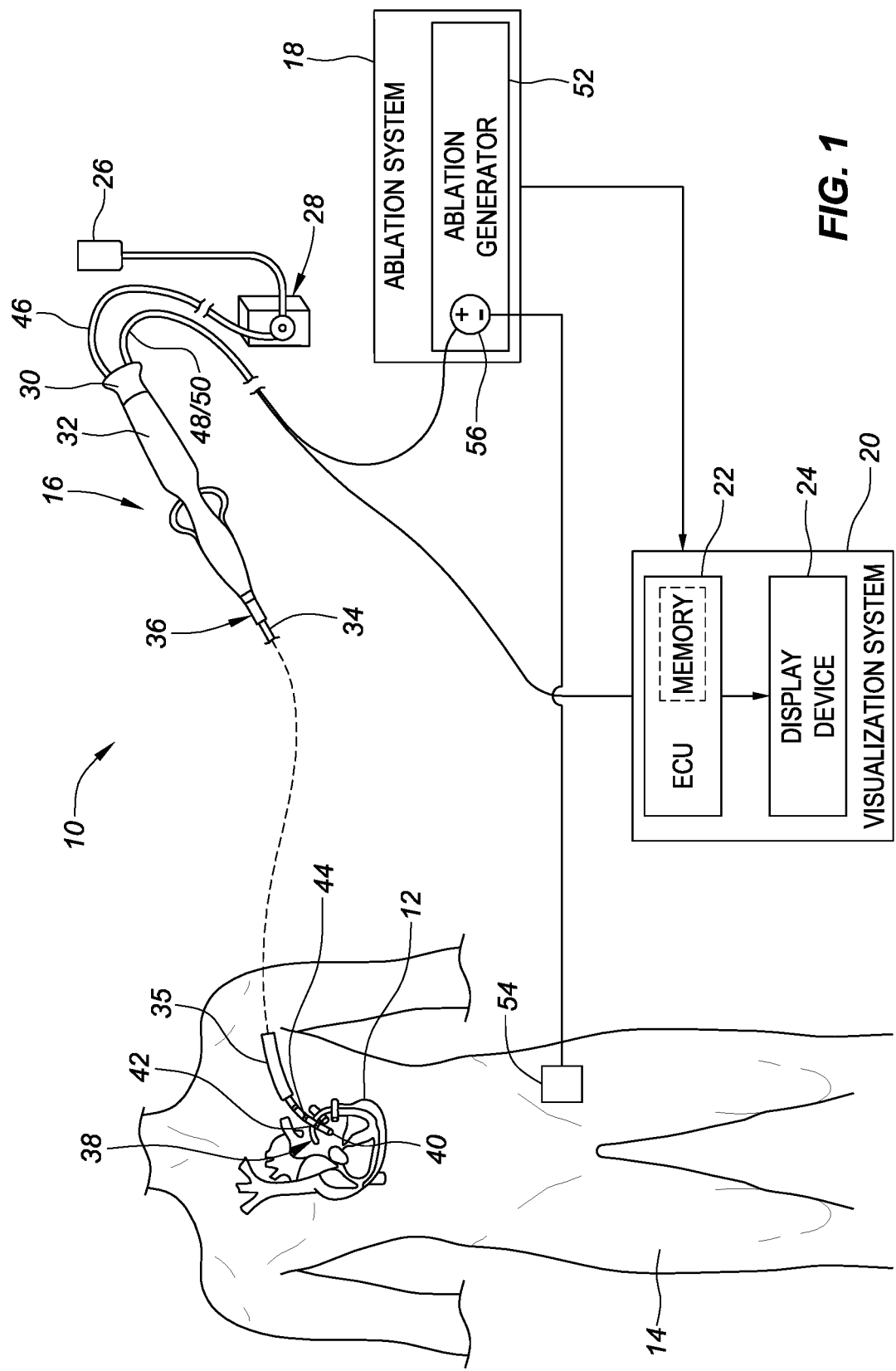
FIG. 1 is a diagrammatic view of a system for performing one more diagnostic and/or therapeutic functions in association with cardiac tissue, according to embodiments of the present disclosure.

Referring now to the drawings wherein like reference numerals are used to identify identical components in the various views, FIG. 1 illustrates one exemplary embodiment of a system 10 for performing one or more diagnostic and/or therapeutic functions in association with the heart or cardiac tissue 12 within a human body 14, according to embodiments of the present disclosure. It should be understood, however, that the system 10 may find application in connection with the ablation of a variety of other tissues within human and non-human bodies.

The system 10 may include a medical device (such as, for example, an electrophysiology catheter 16) an ablation system 18, and/or a system 20 for the visualization, navigation, and/or mapping of internal body structures. The system 20 may include, for example and without limitation, an electronic control unit (ECU) 22 and a display device 24. Alternatively, the ECU 22 and/or the display 24 may be separate and distinct from, but electrically connected to and configured for communication with, the system 20.

With continued reference to FIG. 1, the catheter 16 can be provided for examination, diagnosis, and/or treatment of internal body tissues such as the tissue 12. In an exemplary embodiment, the electrophysiology catheter 16 comprises a diagnostic catheter, such as an electrical mapping catheter that may include a plurality of electrodes configured to monitor one or more electrical signals transmitted throughout the adjacent tissue 12. For example, electrophysiology catheter 16 may comprise a curved high density electrode mapping catheter.

The curved high density electrode mapping catheter may comprise a flexible framework on which a plurality of electrodes are disposed, as further discussed herein. The curved high density electrode mapping catheter can be irrigated in an embodiment such that the catheter 16 may further comprise an inner fluid delivery tubing that may include at least one fluid delivery port. In the exemplary embodiment wherein the catheter 16 is an irrigated catheter, the catheter 16 can be connected to a fluid source 26 providing a biocompatible fluid such as saline, or a medicament, through a pump 28 (which may comprise, for example, a fixed rate roller pump or variable volume syringe pump with a gravity feed supply from the fluid source 26, as shown) for irrigation. It should be understood, however, that catheter 16 is not limited to an irrigated catheter. Rather, in other embodiments, the catheter 16 may comprise an ablation catheter (e.g., radio frequency (RF), cryoablation, ultrasound, etc.) with or without fluid delivery through the catheter.

In an exemplary embodiment where the catheter comprises an ablation catheter, the catheter 16 is electrically connected to the ablation system 18 to allow for the delivery of ablative energy, or the like. The catheter 16 may include a cable connector or interface 30, a handle 32, a shaft 34 having a proximal end 36 and a distal end 38, and one or more electrodes 40, 42 mounted in or on the shaft 34 of the distal portion of catheter 16. In an exemplary embodiment, the electrodes 40, 42 are disposed at or near the distal end portion 38 of the shaft 34, with the electrode(s) 40 comprising an ablation electrode disposed at the extreme distal end portion 38 of the shaft 34 (i.e., tip electrode 40), and the electrode(s) 42 comprising a positioning electrode used, for example, with the visualization, navigation, and mapping system 20. Positioning electrode(s) 42 can be configured to provide a signal indicative of both a position and orientation of at least a portion of the catheter 16. The catheter 16 may further include other conventional components such as, for example and without limitation, a temperature sensor (or sensors) 44, additional electrodes, and corresponding conductors.

The connector 30 provides mechanical, fluid, and electrical connection(s) for cables 46, 48, 50 extending from the pump 28, the ablation system 18, and the visualization, navigation, and/or mapping system 20. The connector 30 is conventional in the art and is disposed at the proximal end 36 of the catheter 16.

The handle 32 provides a location for the clinician to hold the catheter 16 and may further provide means for steering or guiding the shaft 34 within the body 14 as known in the art. Catheter handles 32 are generally conventional in the art and it will be understood that the construction of the handle 32 may vary. In an embodiment, for the purpose of steering the shaft 34 within the body 14, the handle 32 can be substituted by a controllable robotic actuator.

The shaft 34 is an elongate, tubular, flexible member configured for movement within the body 14. The shaft 34 supports, for example and without limitation, one or more electrodes (e.g., electrodes 40, 42), associated conductors, and possibly additional electronics used for signal processing, visualization, localization, and/or conditioning. The shaft 34 may also permit transport, delivery and/or removal of fluids (including irrigation fluids, medicaments, and bodily fluids, etc.), medicines, and/or surgical tools or instruments. The shaft 34 can include one or more lumens configured to house and/or transport electrical conductors, fluids, or surgical tools. The shaft 34 can be introduced into a blood vessel or other structure within the body 14 through a conventional introducer 35. The shaft 34 is then steered or guided through the body 14 to a desired location such as the tissue 12 with pullwires, tension elements, so-called push elements, or other means known in the art.

As generally illustrated in FIG. 1, an ablation system 18 can be comprised of, for example, an ablation generator 52 and one or more ablation patch electrodes 54. The ablation generator 52 generates, delivers, and controls ablation energy (e.g., RF) output by the ablation catheter 16 and the tip electrode 40 thereof, in particular. The generator 52 is conventional in the art and may comprise a commercially available unit sold under the model number IBI-1500T RF Cardiac Ablation Generator, available from St. Jude Medical, Inc. In an exemplary embodiment, the generator 52 may include an RF ablation signal source 56 configured to generate an ablation signal that is output across a pair of source connectors: a positive polarity connector SOURCE (+), which electrically connects to the tip electrode 40 of the catheter 16; and a negative polarity connector SOURCE (−), can be electrically connected to one or more of the patch electrodes 54.

It should be understood that the term connectors as used herein does not imply a particular type of physical interface mechanism, but is rather broadly contemplated to represent one or more electrical nodes (including multiplexed and de-multiplexed nodes). The source 56 is configured to generate a signal at a predetermined frequency in accordance with one or more user specified control parameters (e.g., power, time, etc.) and under the control of various feedback sensing and control circuitry. The source 56 may generate a signal, for example, with a frequency of about 450 kHz or greater for RF energy. The generator 52 may also monitor various parameters associated with the ablation procedure including, for example, impedance, the temperature at the distal tip of the catheter, applied ablation energy, power, force, proximity, and the position of the catheter, and provide feedback to the clinician or another component within the system 10 regarding these parameters.

The visualization, navigation, and/or mapping system 20 with which the positioning electrode 42 can be used may comprise an electric field-based system, such as, for example, that having the model name ENSITE NAVX (aka EnSite Classic as well as newer versions of the EnSite system, denoted as ENSITE VELOCITY) and commercially available from St. Jude Medical, Inc. and as generally shown with reference to U.S. Pat. No. 7,263,397 titled "Method and Apparatus for Catheter Navigation and Location and Mapping in the Heart," the entire disclosure of which is incorporated herein by reference. In accordance with an electric field-based system, the positioning electrode(s) 42 can be configured to be responsive to an electric field transmitted within the body of the patient. The positioning electrode(s) 42 can be used to sense an impedance at a particular location and transmit a representative signal to an external computer or processor. The positioning electrode(s) 42 may comprise one or more ring electrodes in an electric field-based system. In other exemplary embodiments, however, the visualization, navigation, and/or mapping system may comprise other types of systems, such as, for example and without limitation: a magnetic field-based system such as the CARTO System (now in a hybrid form with impedance and magnetically-driven electrodes) available from Biosense Webster, and as generally shown with reference to one or more of U.S. Pat. No. 6,498,944 entitled "Intrabody Measurement," U.S. Pat. No. 6,788,967 entitled "Medical Diagnosis, Treatment and Imaging Systems," and U.S. Pat. No. 6,690,963 entitled "System and Method for Determining the Location and Orientation of an Invasive Medical Instrument," the entire disclosures of which are incorporated herein by reference, or the gMPS system from MediGuide Ltd. of Haifa, Israel (now owned by St. Jude Medical, Inc.), and as generally shown with reference to one or more of U.S. Pat. No. 6,233,476 entitled "Medical Positioning System," U.S. Pat. No. 7,197,354 entitled "System for Determining the Position and Orientation of a Catheter," and U.S. Pat. No. 7,386,339 entitled "Medical Imaging and Navigation System," the entire disclosures of which are incorporated herein by reference.

In accordance with a magnetic field-based system, the positioning electrode(s) 42 can be configured to be responsive to a magnetic field transmitted through the body of the patient. The positioning electrode(s) 42 can be used to sense the strength of the field at a particular location and transmit a representative signal to an external computer or processor. The positioning electrode(s) 42 may comprise one or more metallic coils located on or within the catheter 16 in a magnetic field-based system. As noted above, a combination electric field-based and magnetic field-based system such as the CARTO 3 System also available from Biosense Webster, and as generally shown with reference to U.S. Pat. No. 7,536,218 entitled "Hybrid Magnetic-Based and Impedance-Based Position Sensing," the entire disclosure of which is incorporated herein by reference, can be used. In accordance with a combination electric field-based and magnetic field-based system, the positioning electrodes 42 may comprise both one or more impedance-based electrodes and one or more magnetic coils. Commonly available fluoroscopic, computed tomography (CT), and magnetic resonance imaging (MRI)-based systems can also be used.

Figure 2:
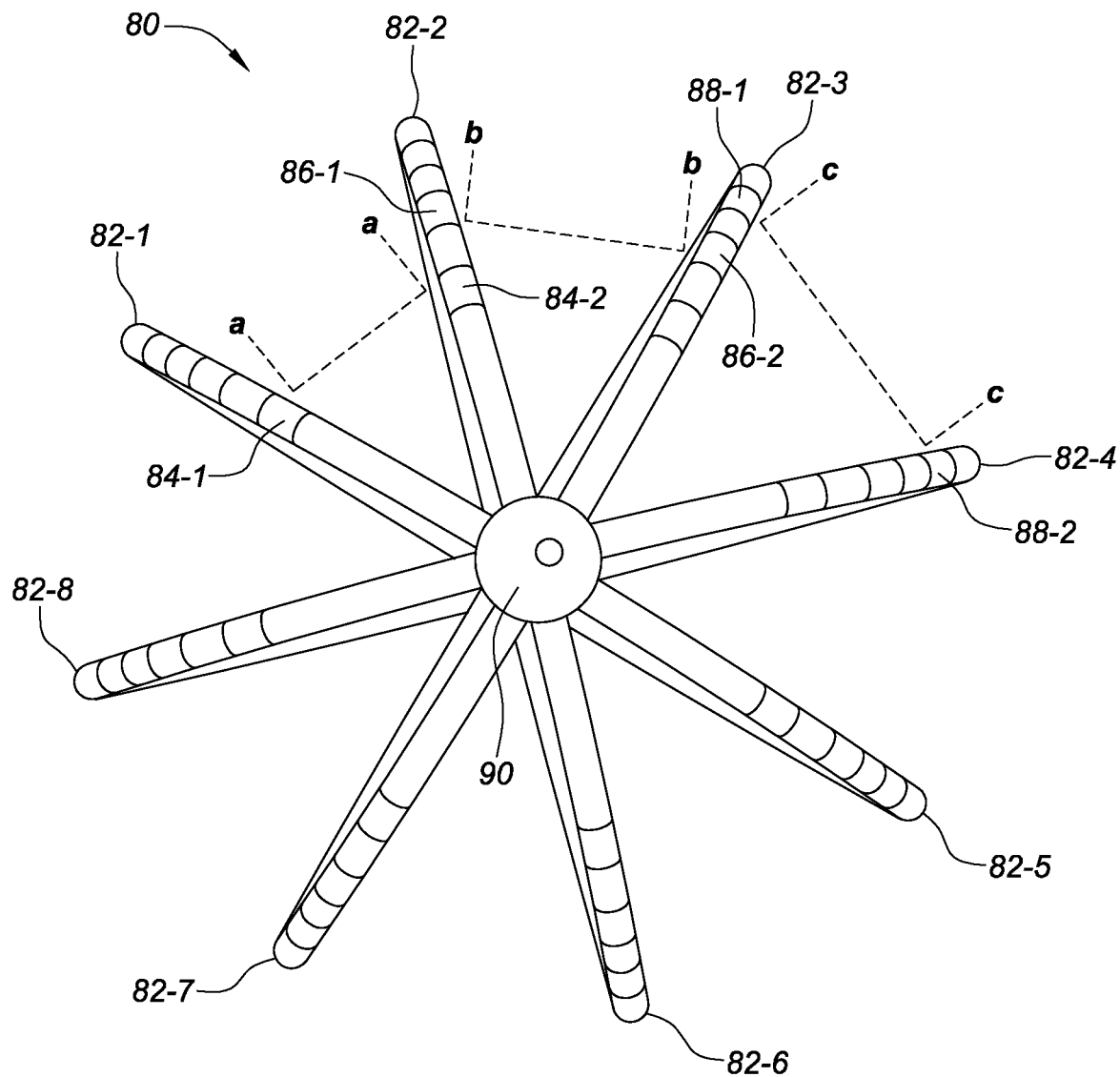
FIG. 2 is a top view of an electrode basket catheter, which illustrates how interelectrode spacing decreases towards proximal and distal poles of an electrode basket catheter.

FIG. 2 is a top view of an electrode basket catheter 80, which illustrates how interelectrode spacing decreases towards proximal and distal poles of the electrode basket catheter 80. The electrode basket catheter 80 is illustrated in an expanded configuration. For example, the electrode basket catheter 80 includes a plurality of splines 82-1, 82-2, . . . , and 82-8, hereinafter referred to in the plural as splines 82, which can be connected at their proximal ends at a proximal pole via a proximal connector (not depicted) and can be connected at their distal ends at a distal pole via a distal connector 90. The proximal connector can be moved in a proximal direction away from the distal connector 90 to collapse the splines 82 and can be moved in a distal direction toward the distal connector 90 to expand the splines 82 into the expanded state, which is depicted.

A plurality of electrodes 84-1, 84-2, 86-1, 86-2, 88-1, 88-2 can be disposed on each one of the splines 82. For ease of reference, only some of the electrodes are referred to herein. In an example, a first ring of electrodes 84-1, 84-2 can be disposed on each one of the splines 82. The first ring of electrodes 84-1, 84-2 can be the most distally disposed electrodes on each one of the splines 82. In an example, a spacing between each one of the first ring of electrodes can be equal. For instance, with respect to the first ring of electrodes 84-1, 84-2, a spacing between the electrodes 84-1, 84-2 can be defined by the line aa. As depicted in FIG. 2, a second ring of electrodes 86-1, 86-2 can be disposed on each one of the splines proximally with respect to the first ring of electrodes 84-1, 84-2 and can have a spacing between the electrodes 86-1, 86-2 defined by the line bb. As further depicted in FIG. 2, a third ring of electrodes 88-1, 88-2 can be disposed on each one of the splines proximally with respect to the first ring of electrodes 84-1, 84-2 and the second ring of electrodes 86-1, 86-2 and can have a spacing between the electrodes 88-1, 86-2 defined by the line cc.

As depicted in FIG. 2, a spacing between each ring of electrodes (i.e., first ring of electrodes 84-1, 84-2, second ring of electrodes 86-1, 86-2, and third ring of electrodes 88-1, 88-2) can be different. For ease of reference, only a portion of the electrodes included in each ring of electrodes are discussed herein. In some embodiments, when sensing electrical signals that are generated by tissue (e.g., cardiac tissue), the different spacing between each of the electrodes in different rings can prove to be problematic and/or at least needs to be accounted for. For example, in some embodiments, timing, velocity, etc. associated with electrical waves passing through cardiac tissue can be determined based on timing associated with electrical signals received via each one of the electrodes. However, since a spacing between the electrodes is not uniform among all of the electrodes disposed on the electrode basket catheter 80, spacing must be accounted for in performing such a calculation. Furthermore, if the electrode basket catheter 80 is to be used for performing ablation, lesion lines created by each ring of electrodes may not be consistently spaced apart from one another, which can decrease an effectiveness and/or consistency of the ablation being performed. Embodiments of the present disclosure can result in a uniform spacing between electrodes disposed on a curved high density electrode mapping catheter.

Figure 3A:
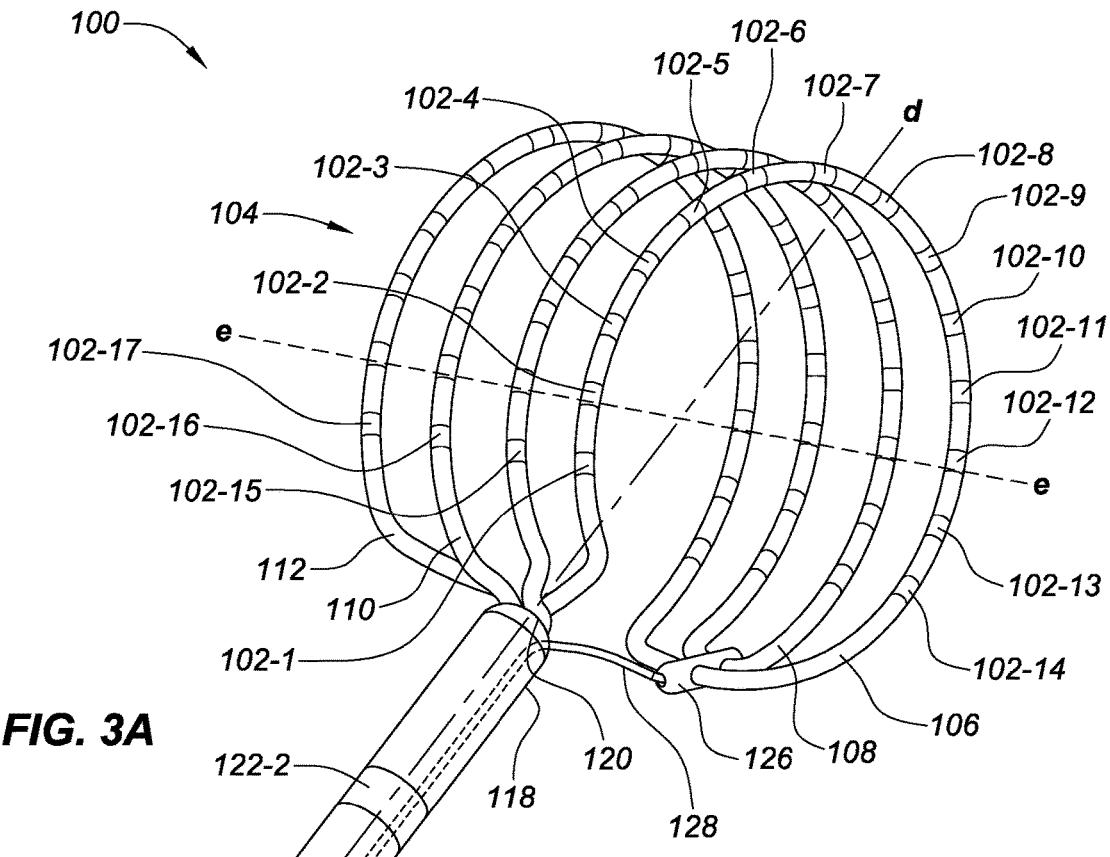
FIG. 3A is an isometric view of a curved high density electrode mapping catheter, in accordance with embodiments of the present disclosure.

FIG. 3A is an isometric view of a curved high density electrode mapping catheter 100, in accordance with embodiments of the present disclosure. The contents of International Application No. PCT/US2014/011940 entitled Flexible High-Density Mapping Catheter Tips and Flexible Ablation Catheter Tips with Onboard High-Density Mapping Electrodes is hereby incorporated by reference as though fully set forth herein. The contents of U.S. application Ser. No. 15/331,562 entitled High Density Electrode Mapping Catheter and U.S. Application No. 62/572,186 entitled Catheter with High-Density Mapping Electrodes are hereby incorporated by reference as though fully set forth herein.

In some embodiments, the curved high density electrode mapping catheter 100 can include a flexible tip portion that is formed from a flexible framework 104. In an example, in some embodiments, the curved high density electrode mapping catheter 100 can include a basket assembly disposed at a distal end of the catheter shaft 114. In some embodiments, the flexible framework 104 can be curved, as depicted in FIG. 3A and further discussed herein. A plurality of electrodes 102-1, 102-2, 102-3, . . . , 102-17 can be disposed on the flexible framework 104, forming a flexible array of electrodes, which can be curved in some embodiments. Although the curved high density electrode mapping catheter 100 includes a plurality of electrodes, for the sake of clarity, only electrodes 102-1, 102-2, 102-3, . . . , 102-17, also referred to herein as microelectrodes, have been labeled in FIG. 3A. Hereinafter, electrodes 102-1, 102-2, 102-3, . . . , 102-17 are referred to in the plural as electrodes 102.

The flexible array (or 'paddle' configuration) of electrodes 102 comprises four side-by-side, arms 106, 108, 110, 112, which can form a flexible framework 104 on which the electrodes 102 are disposed. The four electrode-carrier arms comprise a first outboard arm 106, a second outboard arm 112, a first inboard arm 108, and a second inboard arm 110. These arms can be laterally separated from one another. In some embodiments, the arms 106, 108, 110, 112 can each be equidistant from one another. Although four electrode-carrier arms are depicted, greater than or fewer than four electrode-arms can be included in the flexible array.

In some embodiments, as discussed above, the basket assembly can include a plurality of splines (e.g., arms 106, 108, 110, 112). A plurality of electrodes 102 can be disposed on each one of the splines, such that a distance between adjacent electrodes 102 on each one of the individual splines is of a first distance and a distance between corresponding electrodes 102 disposed on adjacent splines is of a second distance. In some embodiments, the first distance and the second distance can be equal. The basket assembly can include a curved shape and the electrodes can be disposed on the curved shape. In some embodiments, each one of the plurality of splines on the curved shape can be equidistant from one another, resulting in a uniform spacing between neighboring electrodes disposed on each spline.

In some embodiments, the curved high density electrode mapping catheter 100 can include a catheter shaft 114. The catheter shaft 114 can include a proximal end 116 and a distal end 118. The distal end can include a connector 120, which can couple the distal end of the catheter shaft 114 to a proximal end of the flexible framework 104. The catheter shaft 114 can define a catheter shaft longitudinal axis dd, as depicted in FIG. 3A. The catheter shaft 114 can be made of a flexible material, such that it can be threaded through a tortuous vasculature of a patient. In some embodiments, the catheter shaft 114 can include one or more ring electrodes 122-1, 122-2 disposed along a length of the catheter shaft 114. The ring electrodes 122-1, 122-2 can be used for diagnostic, therapeutic, and/or mapping procedures, in an example.

In some embodiments, the flexible framework 104 can be curved about a transverse framework axis ee that is disposed transverse to the catheter shaft longitudinal axis dd. For example, as depicted in FIG. 3A, the transverse framework axis ee is disposed at a 90 degree angle with respect to the catheter shaft longitudinal axis dd. As depicted, each one of the first inboard transition arm 108, second inboard transition arm 110, first outboard transition arm 106, and second outboard transition arm 112 extend along a respective transition arm curved axis. In an example, each one of the respective transition arm curved axes is disposed about the transverse framework axis ee. For instance, each one of the transition arm curved axes and the respective transition arm 106, 108, 110, 112 associated with each one of the transition arm curved axes are revolved around the transverse framework axis ee.

As depicted in FIG. 3A, the longitudinal axis dd is depicted as passing through the transverse framework axis ee. However, in some embodiments, the transverse framework axis can extend above the longitudinal axis dd or below the longitudinal axis dd. For example, as depicted in FIG. 3D, an offset transverse framework axis $ee^{offset-1}$ can be located above the catheter shaft longitudinal axis dd. Although the flexible framework 104 is still depicted as being disposed about the transverse framework axis ee in FIG. 3D, in some embodiments, the flexible framework 104 can be disposed about the offset transverse framework axis $ee^{offset-1}$, located below the catheter shaft longitudinal axis dd. Similarly, as depicted in FIG. 3D, an offset transverse framework axis $ee^{offset-2}$ can be located below the catheter shaft longitudinal axis dd. Although the flexible framework 104 is still depicted as being disposed about the transverse framework axis ee in FIG. 3D, in some embodiments, the flexible framework 104 can be disposed about the offset transverse framework axis $ee^{offset-2}$, located below the catheter shaft longitudinal axis dd.

In some embodiments, while the curvature of the flexible framework 104 can be located above or below the catheter shaft longitudinal axis dd; the curvature of the flexible framework 104 can further and/or alternatively be located/shifted to the left and/or to the right of the catheter shaft longitudinal axis dd. For example, while the flexible framework 104 is depicted as being relatively symmetric across the catheter shaft longitudinal axis dd, the flexible framework can be disposed/shifted by a greater degree to the left or right of the catheter shaft longitudinal axis dd.

With further reference to FIG. 3A, while the flexible framework 104 is depicted as being disposed about the transverse framework axis ee in a circular configuration, the flexible framework 104 can be disposed about the transverse framework axis ee in other types of configurations, as well. For example, the flexible framework 104 can be disposed about the transverse framework axis ee in an elliptical configuration. In some embodiments, the flexible framework 104 can form a biased curved shape. In some embodiments, the particular configuration of the flexible framework 104 can present the electrodes 102 to the tissue in a manner that allows for uniform spacing between the electrodes 102.

In contrast to FIG. 2, the electrodes 102 can be disposed on a curved flexible framework 104, while a constant spacing between the electrodes 102 can be maintained, and the spacing does not increase and/or decrease such as the spacing associated with the device depicted in FIG. 2. For example, when the flexible framework 104 is not under external forces, the spacing between each one of the arms 106, 108, 110, 112 can be maintained and thus the spacing between the electrodes 102 can also be maintained, while presenting the electrodes 102 to tissue in a cylindrical plane configuration (e.g., cylindrical surface 124). Accordingly, embodiments of the present disclosure can provide benefits associated with the electrode basket catheter 80 depicted in FIG. 2 (e.g., presenting the electrodes to a tissue in a curved surface configuration), while maintaining a consistent spacing between the electrodes 102 disposed on the flexible framework 104.

In some embodiments, a same spacing can be maintained between adjacent electrodes on each one of the arms 106, 108, 110, 112 throughout a curvature of the flexible framework 104. For instance, a spacing between each one of the electrodes 102-1, 102-15, 102-16, 102-17 in a first row of electrodes can be maintained throughout each consecutive row of electrodes throughout the curvature of the flexible framework 104. For example, each one of the electrodes 102-2, 102-3, . . . , 102-14 can each be a first electrode in a number of consecutive rows of electrodes (e.g., 13 rows of electrodes 102). The spacing between each electrode 102 in each one of the rows can be maintained throughout the curvature of the flexible framework 104. In some embodiments, a spacing between each electrode 102 on each arm 106, 108, 110, 112 can be the same as a spacing between each electrode 102 in each row of electrodes 102 disposed on the flexible framework 104.

Figure 3B:
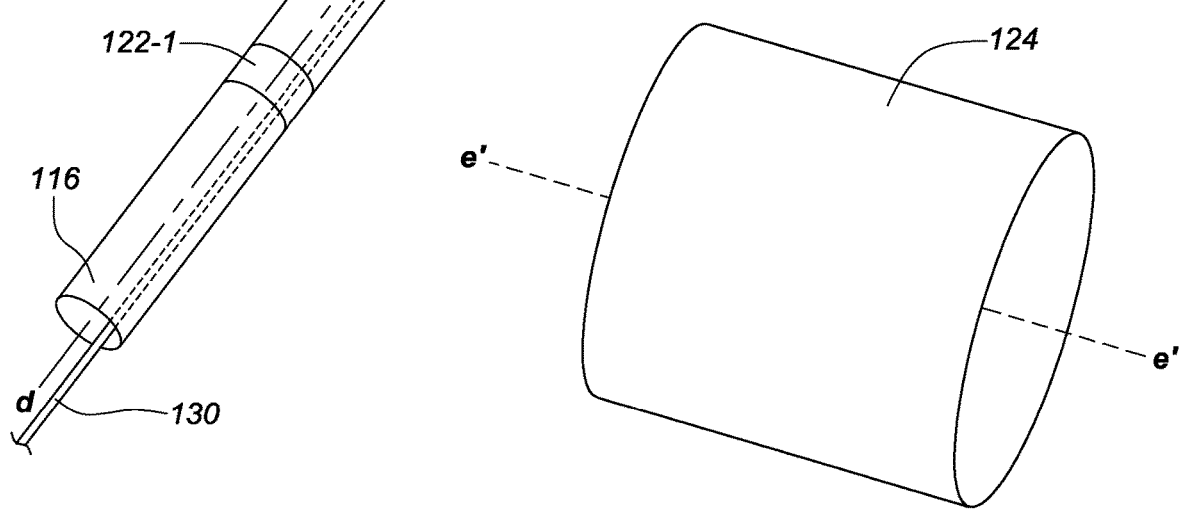
FIG. 3B depicts a cylindrical surface about which a flexible framework of the curved high density electrode mapping catheter in FIG. 3A can be disposed, in accordance with embodiments of the present disclosure.

FIG. 3B depicts a cylindrical surface 124 about which the flexible framework 104 of the curved high density electrode mapping catheter 100 in FIG. 3A can be disposed, in accordance with embodiments of the present disclosure. As further depicted in FIG. 3B, the flexible framework 104 (FIG. 3A) can be disposed about a cylindrical surface 124, which defines a cylindrical axis e'e'. For example, each one of the first inboard transition arm 108, second inboard transition arm 110, first outboard transition arm 106, and second outboard transition arm 112 can be disposed about the cylindrical surface 124, which defines a cylindrical axis e'e'. The cylindrical axis e'e' can be co-axial with the transverse framework axis ee depicted in FIG. 3A, in some embodiments. In an example, the flexible framework 104 can form an arc about the transverse framework axis ee.

Figure 3C:
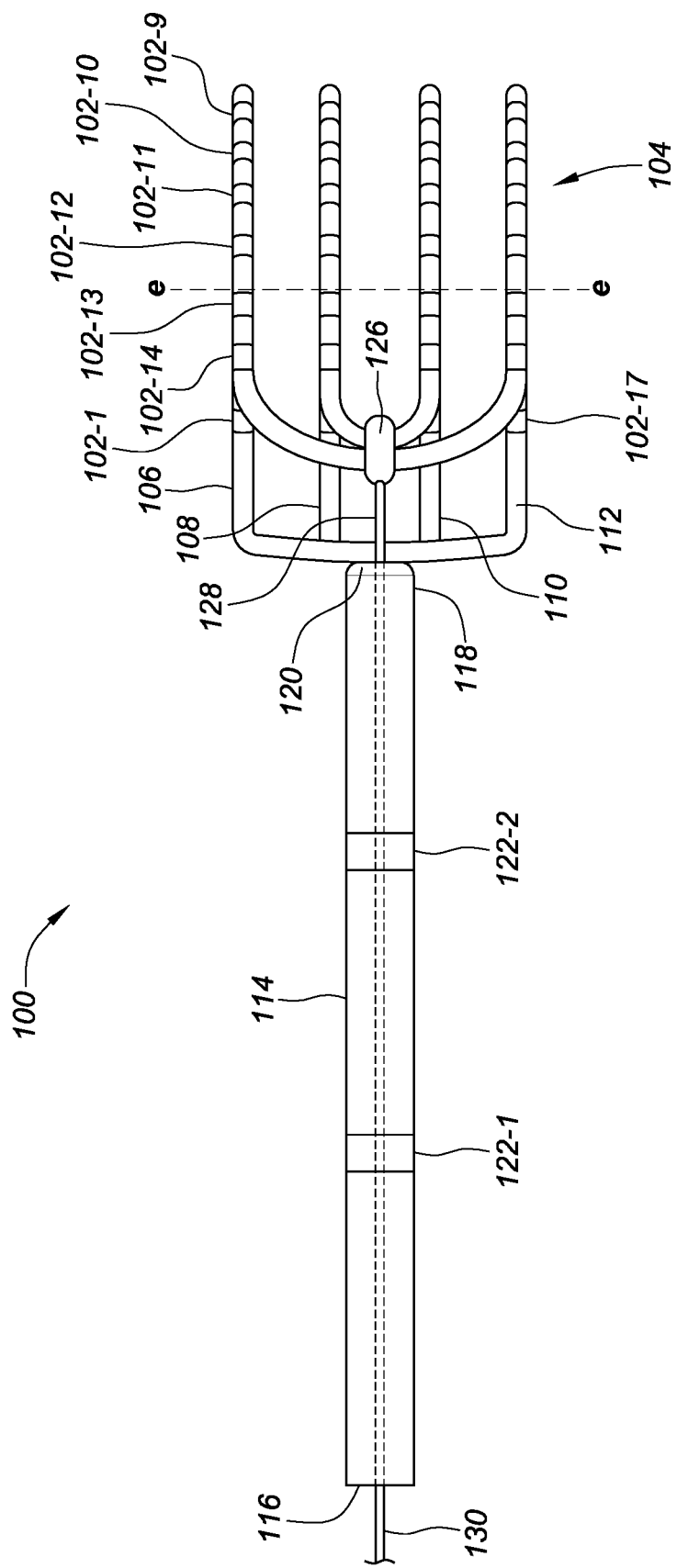
FIG. 3C is a bottom view of the curved high density electrode mapping catheter depicted in FIG. 3A, in accordance with embodiments of the present disclosure.

Each of the four arms can carry a plurality of electrodes 102. For example, each of the four arms can carry electrodes 102 spaced along a length of each of the four arms. Although the curved high density electrode mapping catheter 100 depicted in FIGS. 3A to 3F depict four arms, the curved high density electrode mapping catheter 100 could comprise more or fewer than four arms. Additionally, while the curved high density electrode mapping catheter 100 depicted in FIGS. 3A and 3F depict 56 electrodes disposed on the first outboard arm 106, second outboard arm 112, first inboard arm 108, and second inboard arm 110, catheters can include more or fewer than 56 electrodes disposed on the flexible framework 104. In addition, the first outboard arm 106 and second outboard arm 112 can include more or fewer than 14 electrodes disposed thereon and the first inboard arm 108 and second inboard arm 110 can include more or fewer than 14 electrodes disposed thereon.

In some embodiments, the electrodes 102 can be used in diagnostic, therapeutic, and/or mapping procedures. For example and without limitation, the electrodes 102 can be used for electrophysiological studies, pacing, cardiac mapping, and ablation. In some embodiments, the electrodes 102 can be used to perform unipolar or bipolar ablation. This unipolar or bipolar ablation can create specific lines or patterns of lesions. In some embodiments, the electrodes 102 can receive electrical signals from the heart, which can be used for electrophysiological studies. In some embodiments, the electrodes 102 can perform a location or position sensing function related to cardiac mapping.

The flexible framework 104 can be adapted to conform to tissue (e.g., cardiac tissue). For example, when the flexible framework 104 contacts tissue, the flexible tip portion can deflect, allowing the flexible framework to conform to the tissue. In some embodiments, the arms (or the understructure of the arms) at the distal end of the catheter depicted in FIGS. 3A to 3F are preferably constructed from a flexible or spring-like material such as Nitinol and/or a flexible substrate, as discussed herein. The construction (including, for example, the length and/or diameter of the arms) and material of the arms can be adjusted or tailored to be created, for example, desired resiliency, flexibility, foldability, conformability, and stiffness characteristics, including one or more characteristics that may vary from the proximal end of a single arm to the distal end of that arm (e.g., as the arm wraps around the transverse framework axis ee), or between or among the plurality of arms comprising a single paddle structure. The foldability of materials such as Nitinol and/or flexible substrate provide the additional advantage of facilitating insertion of the flexible framework 104 into a delivery catheter or introducer 35, whether during delivery of the catheter into the body or removal of the catheter from the body at the end of a procedure.

Among other things, the disclosed catheters, with their plurality of electrodes, are useful to (1) define regional propagation maps of particularly sized areas (e.g., one centimeter square areas) within the atrial walls of the heart; (2) identify complex fractionated atrial electrograms for ablation; (3) identify localized, focal potentials between the electrodes for higher electrogram resolution; and/or (4) more precisely target areas for ablation. These mapping catheters and ablation catheters are constructed to conform to, and remain in contact with, cardiac tissue despite potentially erratic cardiac motion. Such enhanced stability of the catheter on a heart wall during cardiac motion provides more accurate mapping and ablation due to sustained tissue-electrode contact. Additionally, the catheters described herein may be useful for epicardial and/or endocardial use. For example, the planar array embodiments depicted herein may be used in an epicardial procedure where the planar array of electrodes is positioned between the myocardial surface and the pericardium. Alternatively, the planar array embodiments may be used in an endocardial procedure to quickly sweep and/or analyze the inner surfaces of the myocardium and quickly create high-density maps of the heart tissue's electrical properties.

In some embodiments, the distal ends of each one of the first outboard arm 106, second outboard arm 112, first inboard arm 108, and second inboard arm 110 can be coupled with one another via a distal junction 126 (e.g., connector). In some embodiments, the connector can be a separate piece to which a distal end of each one of the arms 106, 108, 110, 112 is attached. In some embodiments, however, the arms 106, 108, 110, 112 can be formed from a unitary piece of material, as discussed in U.S. application Ser. No. 15/331,562 entitled High Density Electrode Mapping Catheter, which is incorporated by reference as though fully set forth herein. In such a case, a connector 126 may not be necessary.

In some embodiments, the curved high density electrode mapping catheter 100 can include a tether 128. In some embodiments, the tether 128 can extend through a lumen defined by the catheter shaft 114 from the proximal end 116 through the distal end 118 and can be connected to the connector 126 or a distal end of the arms 106, 108, 110, 112 if the connector 126 is not present. As depicted, in some embodiments, the tether can include a proximal end and a distal end and can extend out of the proximal end 116 of the catheter shaft 114. In some embodiments, the proximal end of the tether 128 can be connected to an actuator, which can be used to apply a particular amount of tension to the tether 128.

Figure 3D:
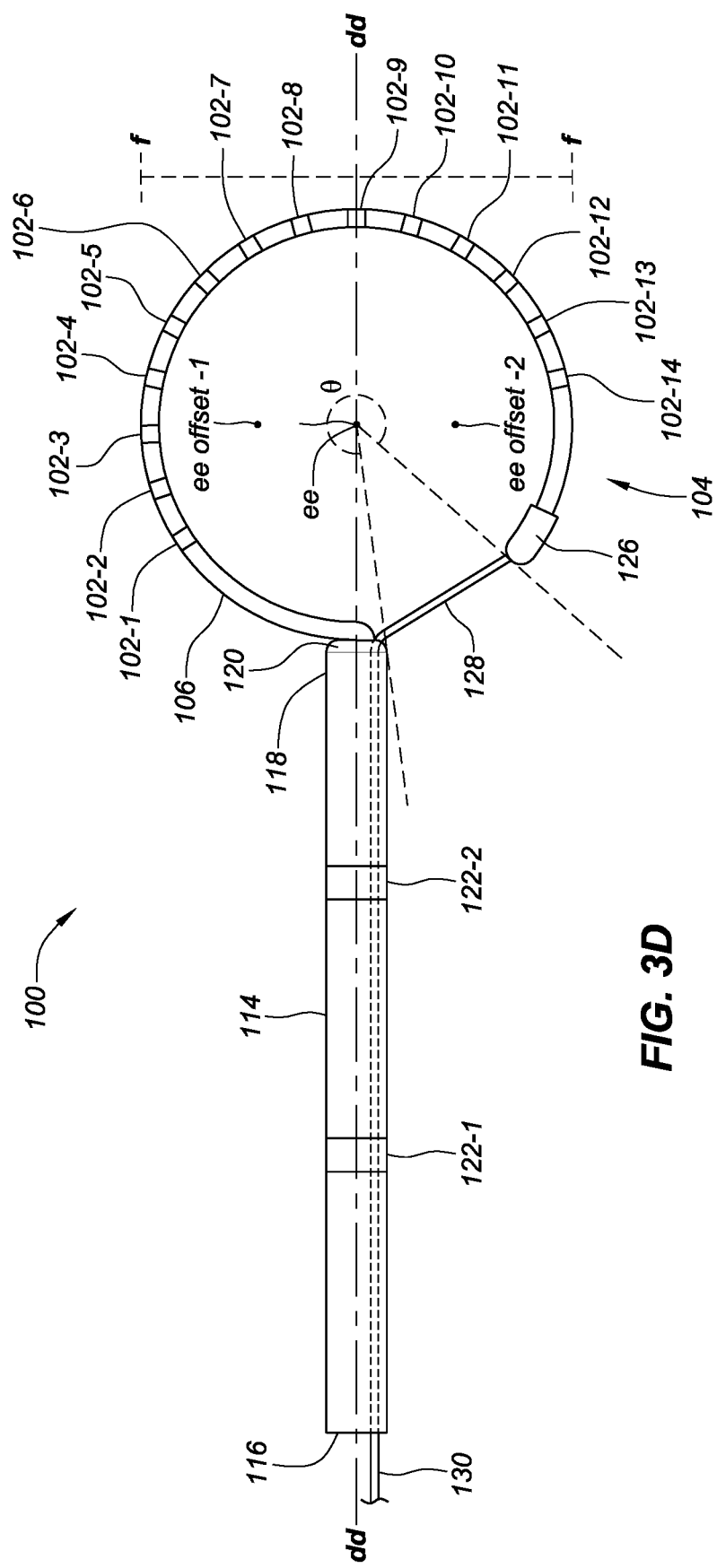
FIG. 3D is a side view of the curved high density electrode mapping catheter depicted in FIGS. 3A and 3C in a deployed state with a first degree of arc, in accordance with embodiments of the present disclosure.
Figure 3E:
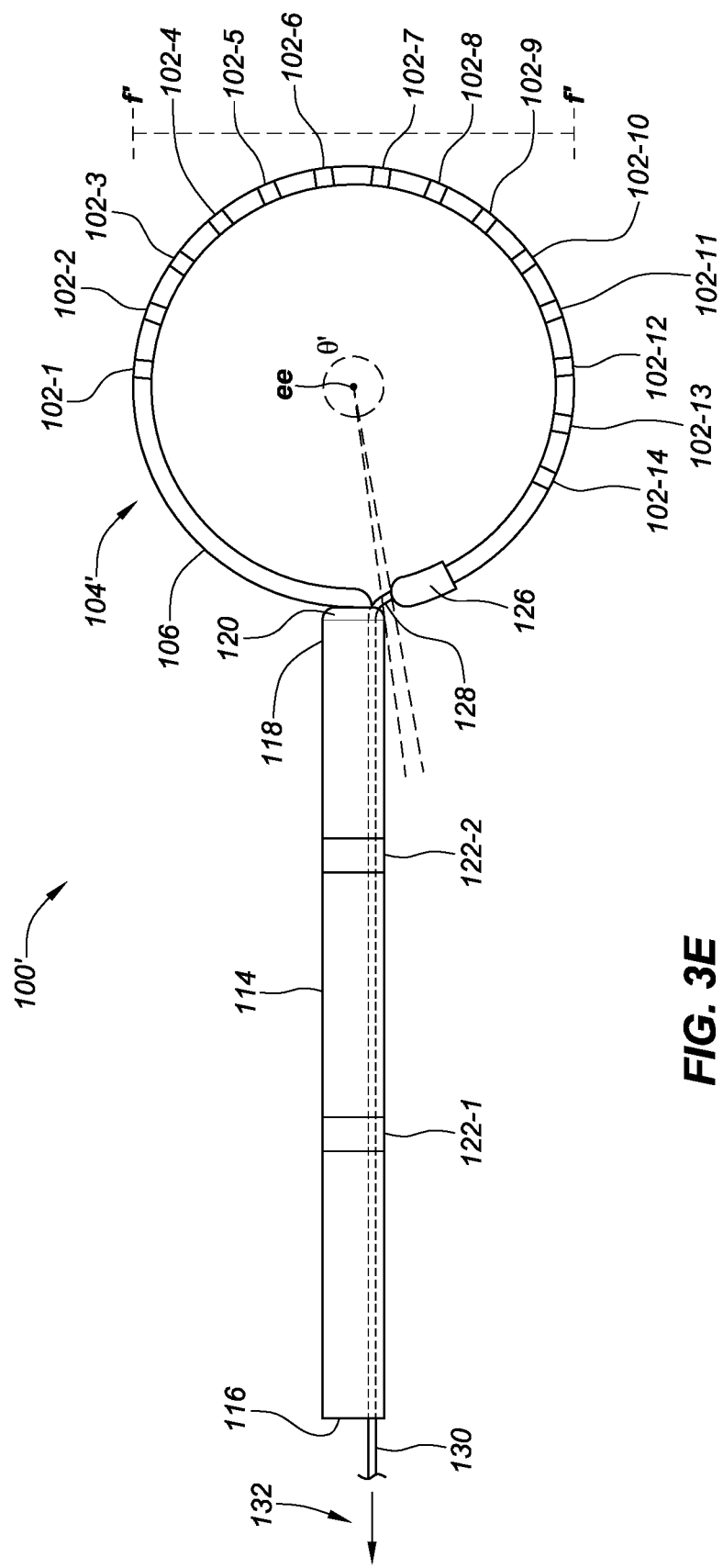
FIG. 3E is a side view of the curved high density electrode mapping catheter 100' depicted in FIGS. 3A, 3C, and 3D in a deployed state with a second degree of arc, smaller than that depicted in FIG. 3D, in accordance with embodiments of the present disclosure.
Figure 3F:
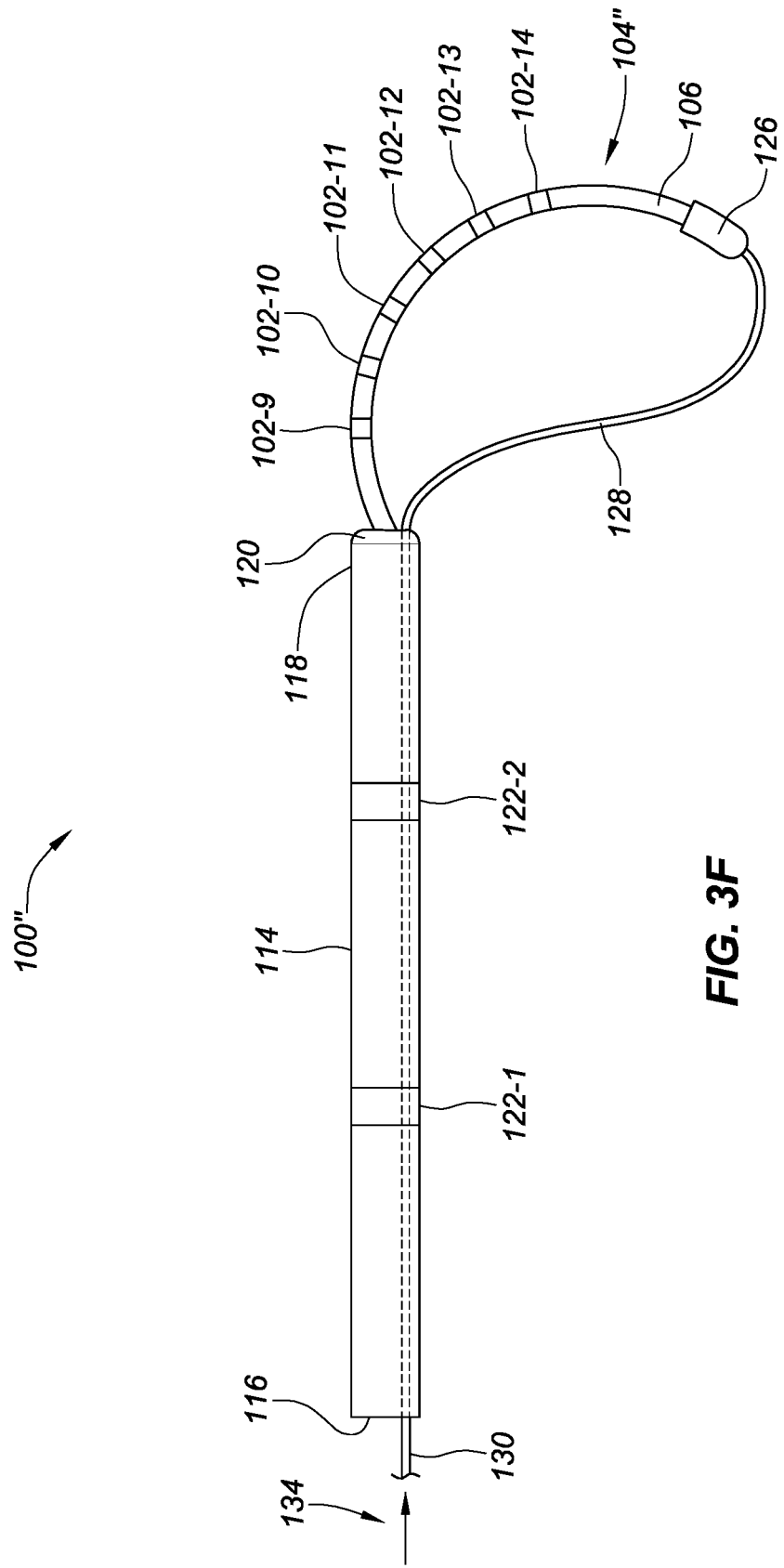
FIG. 3F depicts the curved high density electrode mapping catheter depicted in FIGS. 3A and 3C-3E in a partially retracted state, in accordance with embodiments of the present disclosure.

In some embodiments, upon application of tension to the tether 128, an arc diameter of the transition arms can be increased or decreased, based on the amount of applied tension, as further discussed herein, for example, in relation to FIGS. 3D and 3E. For example, as a proximal end of the tether 130 is pulled proximally in a direction of arrow 132, tension can be applied to the tether 128, causing an arc diameter of the transition arms to be decreased and a degree of arc of the flexible framework to be increased. In some embodiments, the tether 128 can be formed from an elongate flexible material that can resist deformation when a tension is applied to it. For example, the tether 128 can be formed from an elongate flexible material such as a string, wire, cord, strand, thread, etc. In some embodiments, the tether 128 can be formed from a material, such as a fabric, metal, polymer, etc. In some embodiments, the tether 128 can be formed from a material, such as a fabric, metal, polymer, etc. that is braided.

In some embodiments, the tether 128 can be configured to break when a particular force (e.g., tension) is applied to the tether. As previously mentioned, as tension is applied to the tether 128, the distal end of the flexible framework 104 (e.g., the connector 126 if it is used) can be pulled towards the distal end 118 of the catheter shaft 114. This can cause an arc diameter formed by the flexible framework 104 to decrease, as further discussed herein. In some embodiments, however, if enough tension is applied to the tether 128, the connector 126 can be drawn tight against the distal end 118 of the catheter shaft 114 and the connector 120 attached to the distal end 118 of the catheter shaft 114. To prevent damage to the connector 120, distal end 118 of the catheter shaft 114, the connector 126, and/or the distal end of flexible framework 104, the tether 128 can be configured to break at a certain force. In some embodiments, the force at which the tether 128 can be configured to break can be in a range from 1 to 5. In some embodiments, the tether 128 can have a weakened spot located adjacent to the connector 126 such that the tether 128 can break adjacent to the connector 126 and the entire tether 128 can be pulled back into the catheter shaft 114. In some embodiments, the tether 128 can be configured to pull out of the connector 126 when the particular force is applied to the tether 128.

In some embodiments, the flexible framework 104 can be formed from a single piece of material, as previously discussed herein. In an example, the flexible framework 104 can be cut from a single planar (e.g., flat) piece of material. For instance, the flexible framework 104 can be cut from a single planar piece of a shape memory metal, such as nitinol, a flexible substrate, such as a printed circuit board, etc.

In some embodiments, the flexible framework 104 can be curved about the transverse framework axis ee that is disposed transverse to the catheter shaft longitudinal axis dd without application of a force external to the medical device (e.g., curved high density electrode mapping catheter 100). For example, in some embodiments, the flexible framework 104 can be formed from a material that is naturally biased in a curved shape, as further discussed herein, without application of a force external to the curved high density electrode mapping catheter 100. For example, the flexible framework 104 can be curved without application of a force to the flexible framework 104 through contact with a tissue or other solid object. In some embodiments, the flexible framework 104 can be biased in a curved shape via a tether connected to a distal end of the flexible framework 104, as further discussed herein. For example, the tether can be pulled, causing the flexible framework to be pulled (e.g., curved). This force is provided via the curved high density electrode mapping catheter 100, however, and not through contact between the flexible framework 104 and an object, such as a tissue. For example, the flexible framework 104 can be curved about the transverse framework axis ee via a natural bias of the material forming the flexible framework 104 and/or a tether (e.g., tether 128) connected to a distal end of the flexible framework, as further discussed herein.

In some embodiments, the flexible framework 104 made from shape memory metal, such as nitinol can be heat set into the flexible framework 104. In some embodiments, the material that forms the flexible framework 104 can have a natural bias. For example, in some embodiments, the material that forms the flexible framework 104 can have a natural curve to it, thus causing the flexible framework 104 to be naturally curved about the transverse framework axis ee. For example, the flexible framework 104 (e.g., each one of the arms 106, 108, 110, 112) can be naturally biased (e.g., preformed), such that it forms an arc about the transverse framework axis ee, as depicted in FIG. 3A. As a tension is applied to the tether 128, as previously discussed, a degree of the arc can increase as further discussed in relation to FIGS. 3D and 3E.

Although not depicted, in some embodiments, the flexible framework 104 can be naturally biased in a planar state. For example, the flexible framework 104 may have a zero degree of arc in a naturally biased state. However, in some embodiments, the flexible framework 104 can have a particular nonzero degree of arc. For example, as discussed herein, the flexible framework 104 can be naturally biased in a curved configuration. In some embodiments, the tether 128 can be tensioned in the direction of arrow 132 to pull the distal end of the flexible framework 104 towards the distal end 118 of the catheter shaft 114. As such, a bend can be introduced into the flexible framework 104, causing the flexible framework 104 to have a degree of arc, which can be variable depending on an amount of tension applied to the tether 128. In an example, if the tension applied to the tether 128 is reduced, such that the tether 128 moves in a direction opposite of arrow 132, in some embodiments the arc diameter of the transition arms can be increased and the degree of arc of the flexible framework can be decreased.

In some embodiments, as the degree of arc of the flexible framework 104 is varied, a lateral spacing between each one of the arms 106, 108, 110, 112 that form the flexible framework 104 can be maintained. This can be important, as previously alluded to above, because this can allow for the electrodes 102 disposed on each one of the arms 106, 108, 110, 112 to remain evenly spaced with respect to one another. For example, a lateral spacing between each one of the electrodes 102 can remain the same regardless of the degree of arc of the flexible framework.

FIG. 3C is a bottom view of the curved high density electrode mapping catheter 100 depicted in FIG. 3A, in accordance with embodiments of the present disclosure. As further depicted, a distal end of the tether 128 can be connected to the connector 126 and can be routed through a lumen defined by the catheter shaft 114, such that a proximal end 130 of the tether 128 exits a catheter proximal end 116. In some embodiments, as a tension is applied to the proximal end 130 of the tether 128, the connector 126 and the distal end of the flexible framework 104 can be pulled towards the connector 120 disposed on the catheter distal end 118. In an example, the flexible framework 104 depicted in FIG. 3C can be in a naturally biased state, having a particular degree of arc. However, the degree of arc can be increased upon application of tension to the tether 128. As can be seen in FIG. 3C, a lateral spacing between each one of the electrodes 102 disposed on each one of the arms 106, 108, 110, 112 is uniform and can remain uniform regardless of a degree of arc imposed on the arms 106, 108, 110, 112.

FIG. 3D is a side view of the curved high density electrode mapping catheter 100 depicted in FIGS. 3A and 3C in a deployed state with a first degree of arc Θ, in accordance with embodiments of the present disclosure. In some embodiments, the flexible framework 104 of the curved high density electrode mapping catheter 100 can have a variable arc diameter, as discussed herein, depending an amount of tension applied to the tether 128. As depicted in FIG. 3D, the flexible framework 104 defines a first arc diameter, defined by line ff. In some embodiments, the arc diameter of the flexible framework 104 can be increased or decreased with respect to the arc diameter defined by the line ff. For instance, if a tension on the tether 128 is increased, the arc diameter of the flexible framework 104 can be decreased. If a tension on the tether 128 is decreased, the arc diameter of the flexible framework 104 can be increased.

As further depicted with respect to FIG. 3D, a particular degree of arc Θ, represented by Θ, can be defined by the flexible framework 104. For example, as depicted in FIG. 3D, the degree of arc Θ can be approximately 320 degrees. In some embodiments, as discussed with respect to FIG. 3C, the flexible framework 104 can be depicted in FIG. 3D in a naturally biased state. For example, the flexible framework can assume the shape depicted in FIG. 3D with 320 degrees of arc Θ naturally with no tension applied via the tether 128. In some embodiments, however, the flexible framework 104 can naturally assume a shape that has less than 320 degrees of arc Θ or more than 320 degrees of arc Θ. For example, in a natural unbiased state, the flexible framework 104 can have zero degrees of arc Θ and can be disposed along a flat planar surface. In some embodiments, the flexible framework 320 can have a degree of arc Θ in a natural unbiased state in a range from 0 degrees of arc Θ to 360 degrees of arc Θ. In some embodiments, the flexible framework 104 can have a degree of arc Θ in a natural unbiased state in a range from 90 degrees of arc Θ to 330 degrees of arc Θ. In some embodiments, a degree of arc Θ of the flexible framework 104 can be varied as a result of tension being applied to the tether 128. For example, as discussed herein, a degree of arc Θ of the flexible framework 104 can be increased as increased tension is applied to the tether 128 and decreased when decreased tension is applied to the tether 128.

FIG. 3E is a side view of the curved high density electrode mapping catheter 100' depicted in FIGS. 3A, 3C, and 3D in a deployed state with a second degree of arc Θ', greater than that depicted in FIG. 3D, in accordance with embodiments of the present disclosure. As depicted with respect to FIG. 3D, the tether 128 has been retracted proximally, thus causing the connector 128 and the distal end of the flexible framework to be pulled closer to the connector 120 and the catheter distal end 118. As a result, an arc diameter of the flexible framework 104', represented by line f'f' is decreased over the arc diameter of the flexible framework 104, represented by line ff in FIG. 3D. In some embodiments, the flexible framework 104' depicted in FIG. 3E may not be in a naturally biased state. For example, where the flexible framework 104 depicted in FIG. 3D is in a naturally biased state, the flexible framework 104' depicted in FIG. 3E can be forced (e.g., biased) into the depicted state with the second degree of arc Θ' through application of tension to the tether 128. In some embodiments, the flexible framework 104' can be forced (e.g., biased) into the depicted state in FIG. 3E from a planar state. For example, as previously discussed herein, the flexible framework 104' can initially be biased in a planar state and may not have a natural curve/bend to the flexible framework 104'. As a result of tensioning the tether 128, a flexible framework in a planar state with no natural curve/bend can be forced (e.g., biased) into the state depicted in FIG. 3E. In some embodiments, an arc diameter of the flexible framework discussed herein can be in a range from 20 degrees to 180 degrees.

As further discussed in relation to FIG. 3D, the second degree of arc Θ' associated with the flexible framework 104' has been increased through application of tension to the tether 128. In an example, the second degree of arc Θ' is approximately 355 degrees, which is an increase over the first degree of arc Θ by 35 degrees. As a result of the application of tension to the tether 128 and retraction of the tether 128 proximally through the catheter shaft 114, the connector 126 has been moved closer towards the distal end 118 of the catheter shaft, thus resulting in the increased second degree of arc Θ' over that depicted in FIG. 3D.

FIG. 3F depicts the curved high density electrode mapping catheter 100" depicted in FIGS. 3A, 3C-3E in a partially retracted state, in accordance with embodiments of the present disclosure. In some embodiments, the flexible framework 104" can be retracted into a lumen defined by the catheter shaft 114. In an example, as discussed herein, the flexible framework 104" can be formed from a flexible material, which can be folded in on itself to reduce a lateral width of the flexible framework 104", thus allowing the flexible framework to be retracted into the lumen defined by the catheter shaft 114. As depicted in FIG. 3F, the flexible framework 104" can be retracted proximally into the lumen defined by the catheter shaft 114, such that the flexible framework 104" is completely contained within the lumen defined by the catheter shaft 114. As further depicted, a tension applied to the tether 128 can be reduced, such that the tether can move distally through the catheter shaft 114 in the direction of arrow 134, allowing for connector 126 and/or distal end of the flexible framework 104" to swing away from the catheter distal end 114, further allowing for the flexible framework 104" to be drawn into the lumen defined by the catheter shaft 114.

Figure 4:
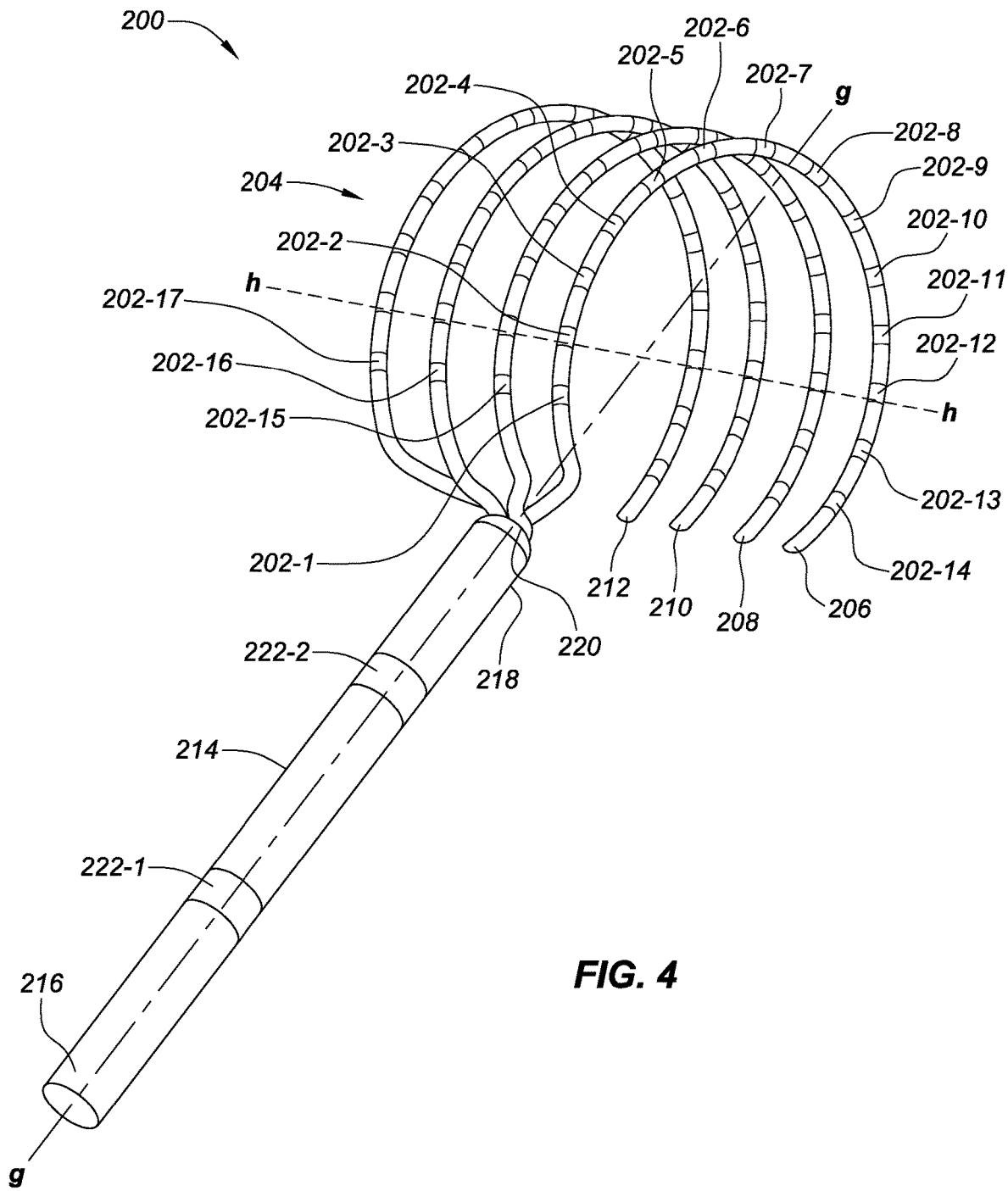
FIG. 4 is an isometric view of a curved high density electrode mapping catheter that includes a framework that is unconnected at its distal end, in accordance with embodiments of the present disclosure.

FIG. 4 is an isometric view of a curved high density electrode mapping catheter 200 that includes a framework that is unconnected at its distal end, in accordance with embodiments of the present disclosure. In some embodiments, the curved high density electrode mapping catheter 200 can include a flexible tip portion that is formed from a flexible framework 204. In some embodiments, the flexible framework 204 can be curved, as depicted in FIG. 3A and further discussed herein. A plurality of electrodes 202-1, 202-2, 202-3, . . . , 202-17 can be disposed on the flexible framework 204, forming a flexible array of electrodes, which can be curved in some embodiments. Although the curved high density electrode mapping catheter 200 includes a plurality of electrodes, for the sake of clarity, only electrodes 202-1, 202-2, 202-3, . . . , 202-17, also referred to herein as microelectrodes, have been labeled in FIG. 4.

Hereinafter, electrodes 202-1, 202-2, 202-3, . . . , 202-17 are referred to in the plural as electrodes 202.

The flexible array (or 'paddle' configuration) of electrodes 202 comprises four side-by-side, arms 206, 208, 210, 212, which can form a flexible framework 204 on which the electrodes 202 are disposed. The four electrode-carrier arms comprise a first outboard arm 206, a second outboard arm 212, a first inboard arm 208, and a second inboard arm 210. These arms can be laterally separated from one another. Although four electrode-carrier arms are depicted, greater than or fewer than four electrode-carrier arms can be included in the flexible array. In contrast to FIGS. 3A to 3F, the electrode-carrier arms may not be connected to one another at their distal ends. In an example, the electrode-carrier arms can be biased naturally such that they assume a curved configuration as depicted in FIG. 4.

In an example, the flexible framework 204 can be protracted and/or retracted from a distal end 218 of a catheter shaft 214, which can also include a proximal end 216. However, in some embodiments, as discussed herein, the flexible framework 204 can be deployed from an introducer into a body. The distal end 218 can include a connector 220, which can couple the distal end 218 of the catheter shaft 214 to a proximal end of the flexible framework 204. The catheter shaft 214 can define a catheter shaft longitudinal axis gg, as depicted in FIG. 4. The catheter shaft 214 can be made of a flexible material, such that it can be threaded through a tortuous vasculature of a patient. In some embodiments, the catheter shaft 214 can include one or more ring electrodes 222-1, 222-2 disposed along a length of the catheter shaft 214. The ring electrodes 222-1, 222-2 can be used for diagnostic, therapeutic, and/or mapping procedures, in an example.

In some embodiments, the flexible framework 204 can be curved about a transverse framework axis ff that is disposed transverse to the catheter shaft longitudinal axis gg. For example, as depicted in FIG. 4, the transverse framework axis hh is disposed at a 90 degree angle with respect to the catheter shaft longitudinal axis gg. As depicted, each one of the first inboard transition arm 208, second inboard transition arm 210, first outboard transition arm 206, and second outboard transition arm 212 extend along a respective transition arm curved axis. In an example, each one of the respective transition arm curved axes is disposed about the transverse framework axis hh. For instance, each one of the transition arm curved axes and the respective transition arm 206, 208, 210, 212 associated with each one of the transition arm curved axes are revolved around the transverse framework axis ff.

As depicted in FIG. 4, the longitudinal axis gg is depicted as passing through the transverse framework axis hh. However, in some embodiments, the transverse framework axis can extend above the longitudinal axis gg or below the longitudinal axis gg, in a manner similar to or the same as that discussed in relation to FIG. 3D, previously discussed herein.

In some embodiments, while the curvature of the flexible framework 204 can be located above or below the catheter shaft longitudinal axis gg; the curvature of the flexible framework 204 can further and/or alternatively be located to the left or to the right of the catheter shaft longitudinal axis gg. For example, while the flexible framework 204 is depicted as being relatively symmetric across the catheter shaft longitudinal axis gg, the flexible framework can be disposed by a greater degree to the left or right of the catheter shaft longitudinal axis gg.

With further reference to FIG. 4, while the flexible framework 204 is depicted as being disposed about the transverse framework axis hh in a circular configuration, the flexible framework 204 can be disposed about the transverse framework axis hh in other types of configurations, as well. For example, the flexible framework 204 can be disposed about the transverse framework axis hh in an elliptical configuration. In some embodiments, the flexible framework 204 can form a biased curved shape. In some embodiments, the particular configuration of the flexible framework 204 can present the electrodes 202 to the tissue in a manner that allows for uniform spacing between the electrodes 202. For example, in contrast to FIG. 2, the electrodes 202 can be disposed on a curved flexible framework 204, while a constant spacing between the electrodes 202 can be maintained, and the spacing does not increase and/or decrease such as the spacing associated with the device depicted in FIG. 2.

Figure 5:
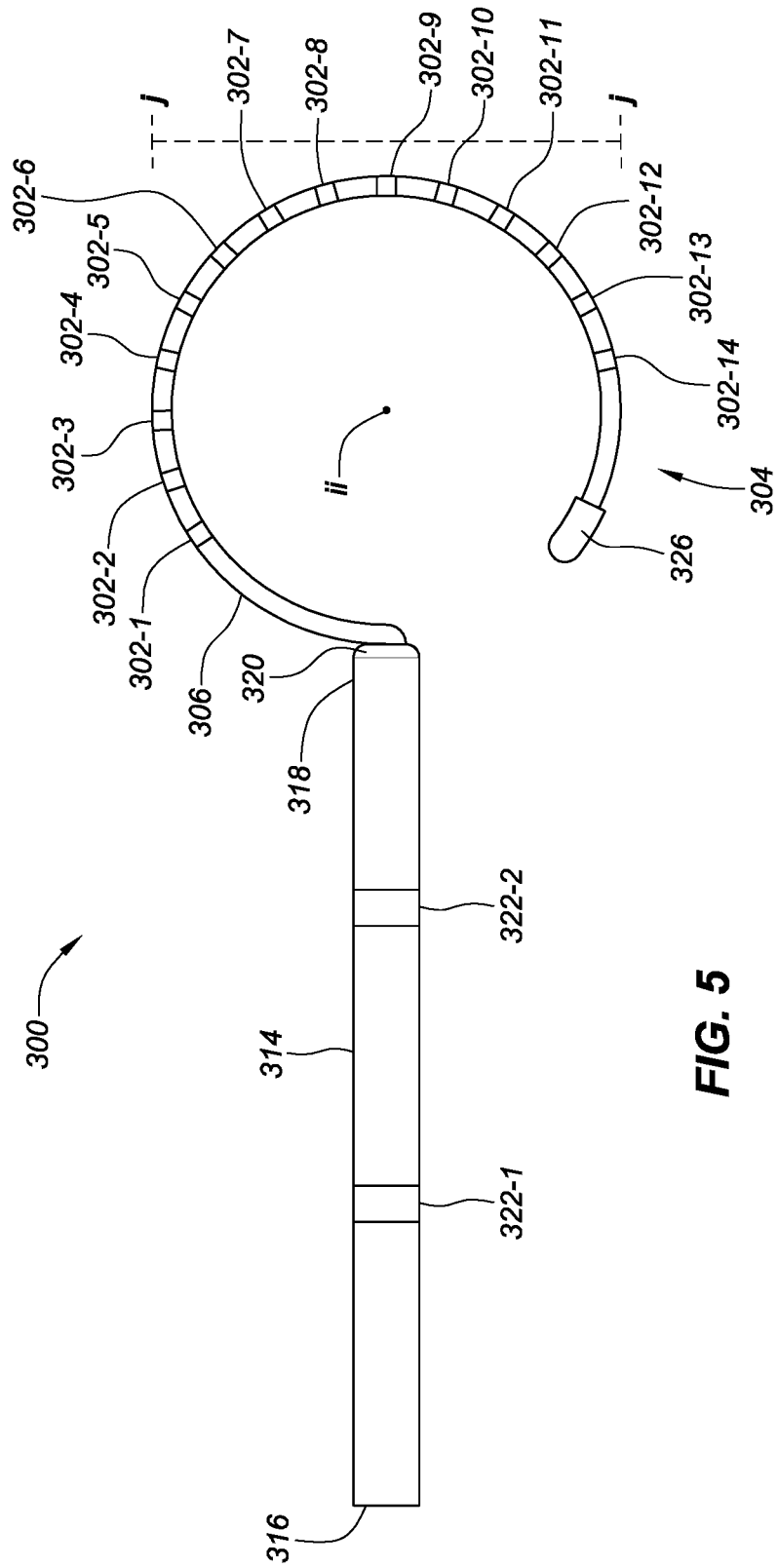
FIG. 5 is a side view of a tetherless curved high density electrode mapping catheter in a deployed state, in accordance with embodiments of the present disclosure.

FIG. 5 is a side view of a tetherless curved high density electrode mapping catheter 300 in a deployed state, in accordance with embodiments of the present disclosure. The tetherless curved high density electrode mapping catheter 300 can include the same or similar features to that discussed in relation to the embodiments depicted in FIGS. 3A to 3F, with the exception that the tetherless catheter 300 does not include a tether. In an example, the tetherless catheter 300 can include a flexible tip portion that is formed from a flexible framework 304. In some embodiments, the flexible framework 304 can be naturally biased in a curved configuration, as depicted in FIG. 5 and further discussed herein. A plurality of electrodes 302-1, 302-2, 302-3, . . . , 302-14 can be disposed on the flexible framework 304, forming a flexible array of electrodes, which can be curved in some embodiments. Although the curved high density electrode mapping catheter 300 includes a plurality of electrodes, for the sake of clarity, only electrodes 302-1, 302-2, 302-3, . . . , 302-14, also referred to herein as microelectrodes, are depicted in FIG. 5. Hereinafter, electrodes 302-1, 302-2, 302-3, . . . , 302-14 are referred to in the plural as electrodes 302.

The flexible array (or 'paddle' configuration) of electrodes 302 comprises four side-by-side arms, of which only arm 306 is visible, which can form a flexible framework 304 on which the electrodes 302 are disposed. The four electrode-carrier arms comprise a first outboard arm 306, a second outboard arm, a first inboard arm, and a second inboard arm, as previously discussed herein. These arms can be laterally separated from one another. In some embodiments, greater than or fewer than four electrode-carrier arms can be included in the flexible array.

In an example, the flexible framework 304 can be protracted and/or retracted from a distal end 318 of a catheter shaft 314, which can also include a proximal end 316. However, in some embodiments, as discussed herein, the flexible framework 304 can be deployed from an introducer into a body. The distal end 318 can include a connector 320, which can couple the distal end 318 of the catheter shaft 314 to a proximal end of the flexible framework 304. The catheter shaft 314 can be made of a flexible material, such that it can be threaded through a tortuous vasculature of a patient. In some embodiments, the catheter shaft 314 can include one or more ring electrodes 322-1, 322-2 disposed along a length of the catheter shaft 314. The ring electrodes 322-1, 322-2 can be used for diagnostic, therapeutic, and/or mapping procedures, in an example.

In some embodiments, the flexible framework 304 can be formed from material (e.g., Nitinol) that can be naturally biased in a curved configuration. Upon deployment of the flexible framework 304 from the catheter shaft 314 and/or from an introducer, the flexible framework 304 can naturally assume a curved configuration. For example, the flexible framework 304 can be naturally biased to assume a curved configuration, such as that depicted in FIG. 5. As depicted, the flexible framework 304 can be disposed about a transverse framework axis ii, as discussed herein. Although a circular configuration is depicted, the flexible framework 304 can be disposed about the transverse framework axis ii in other types of configurations, as well, as further discussed herein. In some embodiments, the axis about which the flexible framework 304 is curved and/or longitudinally extends can be shifted from what is depicted in FIG. 5, as further discussed herein.

Figure 6:
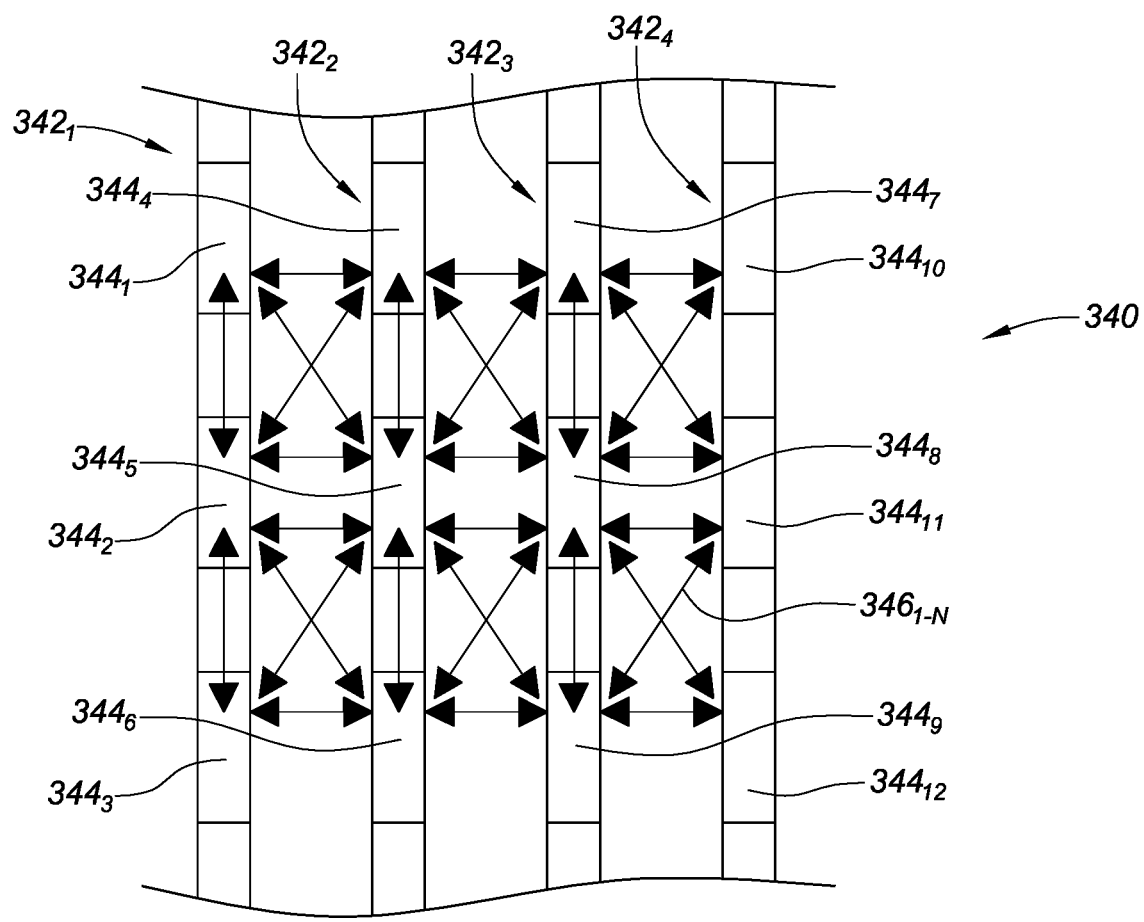
FIG. 6 is a close-up view of a portion of four adjacent arms of a flexible framework, in accordance with various embodiments of the present disclosure.

FIG. 6 is a close-up view of a portion of four adjacent arms $342_1$, $342_2$, $342_3$, $342_4$ of a flexible framework 340, in accordance with various embodiments of the present disclosure. For example, the close-up view of the portion of four adjacent arms $342_1$, $342_2$, $342_3$, $342_4$ of the flexible framework 340 can be similar to or the same as those included on the curved high density electrode mapping catheter 100 depicted in FIG. 3A. Each of the arms 342 includes a number of electrodes $344_{1-12}$ which may be used to sense the electrophysiological characteristics of tissue (often operating in a bipolar configuration with another adjacent electrode), and/or ablate tissue in contact therewith.

The electrodes may ablate tissue using a bipolar configuration, or a uni-polar configuration where one or more of the electrodes are paired with a ground pad which is coupled to a patient's chest, for example. As shown in FIG. 4, a number of bipolar electrode pairings $346_{1-N}$ are shown. These pairings may extend along a longitudinal axis of an arm, transverse to the longitudinal axis of the arm, or the electrode pairings may extend diagonally between two adjacent arms. Such a system may conduct electrophysiology mapping using a bipolar configuration of electrodes across a surface of the flexible framework 340, and/or conduct precise tissue ablation therapies which limit the necrosis of healthy tissue. Further aspects are discussed in U.S. Application No. 62/674,314, titled Radio-Frequency Ablation and Direct Current Electroporation Catheters, which is hereby incorporated by reference, as though fully set forth herein. For example, based on a generated electrophysiology map of tissue in a patient's left atrium, a bipolar ablation therapy may be implemented that ablates only tissue that is susceptible to transmitting stray electrical signals and/or myocardial tissue containing arrhythmic foci (which may generate such electrical signals).

One particular benefit of bipolar ablation therapy is that the actual energy delivered to target tissue is known, due to the close proximity of the positive and negative electrodes. Moreover, bipolar ablation therapy also limits energy delivery to non-target tissue by virtue of the relative proximity of the electrodes.

While FIG. 6 depicts bipole pairs of electrodes which are immediately adjacent to one another, other bipole pair arrangements are readily envisioned. For example, pairs of electrodes that are not immediately adjacent. For example, tissue ablation may be achieved to tissue in proximity to electrodes $344_1$ and $344_{12}$, when the electrodes are operated in a bipolar arrangement. In some embodiments a first number of electrodes (e.g., electrodes $344_{1-3}$) on a first arm $342_1$ may be operated in a bipolar arrangement with a second number of electrodes (e.g., electrodes $344_{4-6}$) on a second arm $342_2$. In yet further embodiments, a first number of electrodes (e.g., electrodes $344_{1-3}$) on a first arm $342_1$ may be operated in a bipolar arrangement with a third number of electrodes (e.g., electrodes $344_{7-9}$) on a third arm $342_3$. Further, a first number of electrodes (e.g., electrodes $344_{1-3}$) on a first arm $342_1$ may be operated in a bipolar arrangement with a fourth number of electrodes (e.g., electrodes $344_{10-12}$) on a fourth arm $342_4$.

Embodiments are described herein of various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it may be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment(s) is included in at least one embodiment. Thus, appearances of the phrases "in various embodiments," "in some embodiments," "in one embodiment," or "in an embodiment," or the like, in places throughout the specification, are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Although at least one embodiment for a high density electrode mapping catheter has been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the devices. Joinder references (e.g., affixed, attached, coupled, connected, and the like) are to be construed broadly and may include intermediate members between a connection of elements and relative movement between elements. As such, joinder references do not necessarily infer that two elements are directly connected and in fixed relationship to each other. It is intended that all matter contained in the above description or shown in the accompanying drawings shall be interpreted as illustrative only and not limiting. Changes in detail or structure may be made without departing from the spirit of the disclosure as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed:

1. A medical device, comprising:
   a catheter shaft having a proximal end and a distal end, wherein a catheter shaft longitudinal axis extends through the proximal end and the distal end;
   a flexible tip portion located adjacent to the distal end of the catheter shaft, wherein the flexible tip portion comprises a flexible framework comprising a plurality of arms, wherein the flexible framework has an unbiased state in which each of the plurality of arms extends circumferentially around a transverse framework axis through a central angle of at least 180 degrees to define an arc length, wherein the transverse framework axis is disposed transverse to the catheter shaft longitudinal axis, and wherein the flexible framework is in the unbiased state in the absence of an external force being applied to the flexible framework;
   a plurality of microelectrodes disposed on the flexible framework and forming a flexible array of microelectrodes adapted to conform to tissue; and
   a tether coupled to a distal end of the flexible framework, wherein the tether passes through a lumen defined by the catheter shaft, wherein the tether is actuatable to pull the distal end of the flexible framework proximally to increase the central angle by which each of the plurality of arms is curved around the transverse framework axis relative to the unbiased state of the flexible framework.

2. The medical device of claim 1, wherein:
   the plurality of arms comprises a first inboard arm, a second inboard arm, a first outboard arm, and a second outboard arm; and
   each of the first inboard arm, the second inboard arm, the first outboard arm, and the second outboard arm extend along have a respective curved centerline that extends circumferentially around the transverse framework axis.

3. The medical device of claim 2, wherein:
   the distal end of the flexible framework comprises a distal end connector;
   the tether is coupled to the distal end connector; and
   each of the first inboard arm, the second inboard arm, the first outboard arm, and the second outboard arm has a respective distal end that is attached to the distal end connector.

4. The medical device of claim 3, wherein the tether is configured to break at the distal end connector when a sufficient force is applied to the tether.

5. The medical device of claim 2, wherein the flexible framework is configured so that a lateral spacing of the first inboard arm, the second inboard arm, the first outboard arm, and the second outboard arm is maintained when the distal end of the flexible framework is pulled proximally by the tether.

6. The medical device of claim 2, wherein the flexible framework is monolithically formed.

7. The medical device of claim 1, wherein the flexible framework is configured to be retracted inside of the lumen defined by the catheter shaft.

8. The medical device of claim 1, wherein each of the plurality of arms extends circumferentially around the transverse framework axis through the central angle of at least 270 degrees to define the arc length in the unbiased state.

9. The medical device of claim 8, wherein each of the plurality of arms extends circumferentially around the transverse framework axis through the central angle of at least 320 degrees to define the arc length in the unbiased state.

10. A medical device, comprising:
    a catheter shaft having a proximal end and a distal end, wherein the catheter shaft defines a central lumen, and wherein a catheter shaft longitudinal axis extends through the proximal end and the distal end;
    a flexible tip portion located adjacent to the distal end of the catheter shaft, wherein the flexible tip portion comprises a flexible framework, wherein the flexible framework comprises a plurality of arms; wherein the flexible framework comprises a distal end connector, wherein each of the plurality of arms has a respective distal end that is attached to the distal end connector; wherein the flexible framework has an unbiased state in which the plurality of arms extends circumferentially around a transverse framework axis through a central angle of at least 180 degrees to define an arc length, wherein the transverse framework axis is disposed transverse to the catheter shaft longitudinal axis, and wherein the flexible framework is in the unbiased state in the absence of an external force being applied to the flexible framework; and
    a plurality of microelectrodes disposed on the flexible framework and forming a flexible array of microelectrodes adapted to be conformable to tissue; and
    a tether coupled to the distal end connector, wherein the tether passes through the central lumen, and wherein the tether is actuatable to pull the distal end connector proximally to increase the central angle that each of the plurality of arms extends circumferentially around the transverse framework axis relative to the unbiased state of the flexible framework.

* * * * *